: US009506914B2

United States Patent
Manger et al.

(10) Patent No.: US 9,506,914 B2
(45) Date of Patent: *Nov. 29, 2016

(54) RECIRCULATING FLUIDIC NETWORK AND METHODS FOR USING THE SAME

(71) Applicant: Fluidigm Corporation, South San Francisco, CA (US)

(72) Inventors: Ian D. Manger, San Francisco, CA (US); Joseph W. Barco, San Francisco, CA (US); Hany R. Nassef, San Mateo, CA (US)

(73) Assignee: Fluidigm Corporation, South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/535,162

(22) Filed: Nov. 6, 2014

(65) Prior Publication Data

US 2015/0168385 A1    Jun. 18, 2015

Related U.S. Application Data

(63) Continuation of application No. 13/434,539, filed on Mar. 29, 2012, now Pat. No. 8,883,092, which is a continuation of application No. 10/602,489, filed on Jun. 23, 2003, now Pat. No. 8,168,139.

(60) Provisional application No. 60/391,292, filed on Jun. 24, 2002.

(51) Int. Cl.
*B81B 3/00* (2006.01)
*G01N 33/53* (2006.01)
(Continued)

(52) U.S. Cl.
CPC ....... *G01N 33/5304* (2013.01); *B01L 3/50273* (2013.01); *B01L 3/502738* (2013.01);
(Continued)

(58) Field of Classification Search
CPC ....................................... B81B 3/00

USPC ................................. 422/502–505
See application file for complete search history.

(56) References Cited

U.S. PATENT DOCUMENTS 6,352,838 B1   3/2002   Krulevitch et al.
6,508,988 B1   1/2003   Van Dam et al.
(Continued)

FOREIGN PATENT DOCUMENTS

EP    846776      6/1998
JP    9-043251    2/1997
(Continued)

OTHER PUBLICATIONS

Jackman, Rebecca J. et al., "Design and Fabrication of Topologically Complex, Three-Dimensional Microstructures," Science, vol. 280, pp. 2089-2091, Jun. 26, 1998.
(Continued)

*Primary Examiner* — Paul Hyun
(74) *Attorney, Agent, or Firm* — Kilpatrick Townsend & Stockton LLP

(57) ABSTRACT

A microfluidic device includes a plurality of first flow channels and a plurality of second flow channels, each such second flow channel intersecting multiple of the first flow channels to define intersecting volumes and a plurality of looped flow channels that each include segments of the flow channels between the intersecting volumes to define a closed loop. The microfluidic device also includes a plurality of control valves each such control valve having a control channel and a deformable segment disposed to restrict flow through a respective one of the first and second flow channels in response to an actuation force applied to the control channel to deflect the deformable segment. The microfluidic device further includes a pump operatively disposed to regulate flow through one of the looped flow channels to regulate flow by the recirculating pump.

28 Claims, 20 Drawing Sheets

(51) Int. Cl.
| | |
|---|---|
| F04B 19/00 | (2006.01) |
| F04B 43/02 | (2006.01) |
| F16K 99/00 | (2006.01) |
| G01N 33/543 | (2006.01) |
| B01L 3/00 | (2006.01) |

(52) U.S. Cl.
CPC ............. *F04B19/006* (2013.01); *F04B 43/02* (2013.01); *F16K 99/0001* (2013.01); *F16K 99/0026* (2013.01); *F16K 99/0036* (2013.01); *F16K 99/0046* (2013.01); *F16K 99/0051* (2013.01); *F16K 99/0059* (2013.01); *G01N 33/54366* (2013.01); *B01L 3/5025* (2013.01); *B01L 3/502707* (2013.01); *B01L 2300/0636* (2013.01); *B01L 2300/0645* (2013.01); *B01L 2300/088* (2013.01); *B01L 2300/0816* (2013.01); *B01L 2300/0861* (2013.01); *B01L 2300/0887* (2013.01); *B01L 2400/0415* (2013.01); *B01L 2400/0481* (2013.01); *B01L 2400/0655* (2013.01); *B81B 3/00* (2013.01); *F16K 99/0003* (2013.01); *F16K 2099/008* (2013.01); *F16K 2099/0074* (2013.01); *F16K 2099/0078* (2013.01); *F16K 2099/0084* (2013.01); *Y10T 436/2575* (2015.01)

(56) References Cited

U.S. PATENT DOCUMENTS

| | | |
|---|---|---|
| 8,168,139 B2 | 5/2012 | Manger et al. |
| 8,883,092 B2 | 11/2014 | Manger et al. |
| 2002/0037499 A1 | 3/2002 | Quake et al. |
| 2002/0102577 A1 | 8/2002 | Raillard et al. |
| 2002/0145231 A1 | 10/2002 | Hansen et al. |
| 2003/0008411 A1 | 1/2003 | Van Dam et al. |
| 2003/0119177 A1 | 6/2003 | Gruber et al. |

FOREIGN PATENT DOCUMENTS

| | | |
|---|---|---|
| WO | WO 96/27025 | 9/1996 |
| WO | WO 00/70082 | 11/2000 |
| WO | WO 01/34302 | 5/2001 |
| WO | WO 01/54843 | 6/2001 |
| WO | WO 01/89695 | 11/2001 |

OTHER PUBLICATIONS

Khandurina, J. et al. "Bioanalysis in Microfluidic Devices," Journal of Chromatography A, vol. 943, Ino. 2, Jan. 18, 2002, Elsevier Science B.V., pp. 159-183.

Chang, Jun Keun et al., "Functional Integration of Serial Dilution and Capillary Electrophoresis on a PDMS Microchip," Biotechnology and Bioprocess Engineering, vol. 8, No. 4, pp. 233-239, 2003.

Chaudhari et al., "Transient Liquid Crystal Thermometry of Microfabricated PCR Vessel Arrays," J. Microelectromechanical Systems, 7(4), pp. 345-355, 1998.

Chee, Mark et al., "Accessing Genetic Information With High-Density DNA Arrays," Science, vol. 274, pp. 610-614, Oct. 25, 1996.

Chen, Chihchen et al., "Gray-Scale Photolithography Using Microfluidic Photomasks," PNAS, vol. 100, No. 4, pp. 1499-1504, Feb. 18, 2003.

Chiang, Yuh-Min et al., "Characterizing the Process of Cast Molding Microfluidic Systems," SPIE, vol. 3877, pp. 303-311, Sep. 1999.

Chiem, N. H. et al., "Microchip Systems for Immunoassay: An Integrated Immunoreactor With Electrophoretic Separation for Serum Theophylline Determination," Clinical Chemistry, vol. 44, No. 3, p. 591, 1998.

Chiou et al., "A Closed-Cycle Capillary Polymerase Chain," Anal. Chem., vol. 73, pp. 2018-2021, 2001.

Chiu, Chi-Sung et al., "Single Molecule Measurements Calibrate Green Fluorescent Protein Surface Densities on Transparent Beads for Use With 'Knock-In' Animals and Other Expression Systems," Journal of Neuroscience Methods, vol. 105, pp. 55-63, 2001.

Chiu, Daniel T. et al., "Patterned Deposition of Cells and Proteins Onto Surfaces by Using Three-Dimensional Microfluidic Systems," PNAS, vol. 97, No. 6, pp. 2408-2413, Mar. 14, 2000.

Chou, Hou-Pu et al., "A Microfabricated Device for Sizing and Sorting DNA Molecules," Proc. Natl. Acad. Sci., vol. 96, pp. 11-13, Jan. 1999.

Chou, Hou-Pu et al., "A Microfabricated Rotary Pump," Biomedical Microdevices, vol. 3, No. 4, pp. 323-330, 2001.

Chou, Hou-Pu et al., "Disposable Microdevices for DNA Analysis and Cell Sorting," Proc. Solid-State Sensor and Actuator Workshop, Hilton Head, South Carolina, pp. 11-14, Jun. 8-11, 1998.

Chou, Hou-Pu et al., "Integrated Elastomer Fluidic Lab-On-A-Chip-Surface Patterning and DNA Diagnostics," Proceedings of the Solid State Actuator and Sensor Workshop, Hilton Head, South Carolina, 4 pages, 2000.

Chou, Hou-Pu, "Microfabricated Devices for Rapid DNA Diagnostics," Doctoral Thesis, California Institute of Technology, pp. i-xii and 1-106, May 30, 2000.

Chou, Hou-Pu et al., "Microfabricated Devices for Sizing DNA and Sorting Cells," Micro- and Nanofabricated Structures and Devices for Biomedical Environmental Applications, Proceedings of SPIE, vol. 3258, pp. 181-187, 1998.

Chou, Hou-Pu et al., "Multiple Disease Diagnostics on a Single Chip," Biophysics Lab, Caltech, pp. 1-4, Mar. 1, 2000.

Costerton, J. William et al., "Microbial Biofilms," Annu. Rev. Microbiol., vol. 49, pp. 711-745, 1995.

Cowen, S. et al., "An On-Chip Miniature Liquid Chromatography System: Design, Construction and Characterization," Micro Total Analysis Systems, Proceedings of the µTAS '94 Workshop, University of Twente, the Netherlands, pp. 2 cover pages and 295-298, 1995.

Crosland-Taylor, P. J., "A Device for Counting Small Particles Suspended in a Fluid Through a Tube," Nature, vol. 171, pp. 37-38, Jan. 3, 1953.

Davila, Herman Moreno, "Molecular and Functional Diversity of Voltage-Gated Calcium Channels," Annals of the New York Academy of Sciences, vol. 868, pp. cover, 102-117, 1999.

Delamarche, Emmanuel et al., "Patterned Delivery of Immunoglobulins to Surfaces Using Microfluidic Networks," Science, vol. 276, pp. 779-781, May 2, 1997.

Delisa, Matthew P. et al., "Mapping Stress-Induced Changes in Autoinducer AI-2 Production in Chemostat-Cultivated *Escherichia coli* K-12," Journal of Bacteriology, vol. 183, No. 9, pp. 2918-2928, May 2001.

Dharmatilleke, Saman et al., "Three-Dimensional Silicone Device Fabrication and Interconnection Scheme for Microfluidic Applications Using Sacrificial Wax Layers," Micro-Electro-Mechanical Systems (MEMS), vol. 2, pp. 413-418, 2000.

Drmanac, R. et al., "DNA Sequence Determination by Hybridization: A Strategy for Efficient Large-Scale Sequencing," Science, vol. 260, pp. 1649-1652, Jun. 11, 1993.

Goodwin, Peter M. et al., "Rapid Sizing of Individual Fluorescently Stained DNA Fragments by Flow Cytometry," Nucleic Acids Research, vol. 21, No. 4, pp. 803-806, 1993.

Granjeaud, Samuel et al., "Expression Profiling: DNA Arrays in Many Guises," BioEssays, vol. 21, pp. 781-790, 1999.

Gravesen, Peter et al., "Microfluidics—A Review," J. Micromech. Microeng., vol. 3, pp. 168-192, 1993.

Greene, Chana, "Characterizing the Properties of PDMS," pp. 1-11, Summer 2000.

Grover, William H. et al., "Monolithic Membrane Valves and Diaphragm Pumps for Practical Large-Scale Integration Into Glass Microfluidic Devices," Sensors and Actuators B, vol. 89, pp. 315-323, 2003.

Guérin, L. J. et al., "Simple and Low Cost Fabrication of Embedded Micro-Channels by Using a New Thick-Film Photoplastic," Transducers '97, 1997 International Conference on Solid-State Sensors and Actuators, Chicago, Illinois, pp. 1419-1422, Jun. 18-19, 1997.

(56) References Cited

OTHER PUBLICATIONS

Guerra, Patricia I. et al., "PEGylation Prevents the N-Terminal Degradation of Megakaryocyte Growth and Development Factor," Pharmaceutical Research, vol. 15, No. 12, pp. 1822-1827, 1998.
Gunderson, Kevin L. et al., "Mutation Detection by Ligation to Complete n-mer DNA Arrays," Genome Research, vol. 8, pp. 1142-1153, 1998.
Guo, Zhen et al., "Enhanced Discrimination of Single Nucleotide Polymorphisms by Artificial Mismatch Hybridization," Nature Biotechnology, vol. 15, pp. 331-335, Apr. 1997.
Hancock, Robert E. W., "A Brief on Bacterial Biofilms," Nature Genetics, vol. 29, p. 360, Dec. 2001.
Hanes, Jozef, et al., "In Vitro Selection and Evolution of Functional Proteins by Using Ribosome Display," Proc. Natl. Acad. Sci. USA, vol. 94, pp. 4937-4942, May 1997.
Hansen, Carl. L. et al., "A Robust and Scalable Microfluidic Metering Method That Allows Protein Crystal Growth by Free Interface Diffusion," PNAS, vol. 99, No. 26, pp. 16531-16536, Dec. 24, 2002.
Hansen, Carl. L. et al., "Systematic Investigation of Protein-Phase Behavior With a Microfluidic Formulator," PNAS Early Edition, 6 pages, 2004.
Harrison, D. Jed et al., "Integration of Analytical Systems Incorporating Chemical Reactions and Electrophoretic Separation," Micro Total Analysis Systems, Proceedings of the μTAS '94 Workshop, University of Twente, the Netherlands, pp. 2 cover pages and 105-111, 1995.
Harrison, D. Jed et al., "Micromachining a Miniaturized Capillary Electrophoresis-Based Chemical Analysis System on a Chip," Science, vol. 261, pp. 895-897, Aug. 13, 1993.
Henion, Jack et al., "Capillary Electrophoresis/Mass Spectrometry: From One Meter Capillaries to Chip-Based Devices," 2 pages, 1999.
Heo, Jinseok et al., "A Microfluidic Bioreactor Based on Hydrogel-Entrapped *E. coli*: Cell Viability, Lysis, and Intracellular Enzyme Reactions," Analytical Chemistry, vol. 75, No. 1, pp. 22-26, Jan. 1, 2003.
Herbert, D., "Continuous Culture of Bacteria," The Journal of General Microbiology, vol. 15, pp. 2 cover pages and iv, 1956.
Herbert, D., "Continuous Culture of Bacteria: Principles and Applications," Chemistry and Industry, pp. 381, Mar. 29, 1958.
Hermanson, Greg T. et al., "Chapter 2—Activation Methods," Immobilized Affinity Ligand Techniques, Academic Press, pp. 2 cover pages, 51-136, 1992.
Hicks, Jennifer, "Genetics and Drug Discovery Dominate Microarray Research," R&D Magazine, pp. 28-33, Feb. 1999.
Hoffmuller, Ulrich et al., "In Vitro Evolution and Selection of Proteins: Ribosome Display for Larger Libraries," Angew. Chem. Int. Ed., vol. 37, No. 23, pp. 3241-3243, 1998.
Hofmann, Oliver et al., "Modular Approach to Fabrication of Three-Dimensional Microchannel Systems in PDMS—Application to Sheath Flow Microchips," Lab on a Chip, vol. 1, pp. 108-114, 2001.
Hoheisel, Jorg D., "Sequence-Independent and Linear Variation of Oligonucleotide DNA Binding Stabilities," Nucleic Acids Research, vol. 24, No. 3, pp. 430-432, 1996.
Hong, Jong Wook et al., "A Nanoliter-Scale Nucleic Acid Processor With Parallel Architecture," Nature Biotechnology, vol. 22, No. 4, pp. 1-5, Apr. 2004.
Hong et al., "Integration of Gene Amplification and Capillary Gel Electrophoresis on a Polydimethylsiloxane-Glass Hybrid Microchip," Electrophoresis, vol. 22, pp. 328-333, 2001.
Hopfgartner, Gerard et al., "Exact Mass Measurement of Product Ions for the Structural Elucidation of Drug Metabolites With a Tandem Quadrupole Orthogonal-Acceleration Time-of-Flight Mass Spectrometer," Journal of the American Society for Mass Spectrometry, vol. 10, pp. cover, 1305-1314, Dec. 1999.
Horn, Howard, "Lab Chips Sector: Microtechnologies Are Changing Healthcare and More," Life Sciences, pp. 19-21, Mar. 20, 2001.
Hornbeck, Larry J. et al., "Bistable Deformable Mirror Device," Spatial Light Modulators and Applications 1988 Technical Digest Series, vol. 8, Postconference Edition, pp. cover, 107-110, Jun. 15-17, 1988.
Hosokawa, Kazuo et al., "A Microfluidic Device for Mixing of Capillary-Driven Liquids," IEEJ Trans. SM, vol. 123, No. 1, pp. 23-24, 2003.
Hosokawa, Kazuo et al., "Droplet-Based Nano/Picoliter Mixer Using Hydrophobic Microcapillary Vent," 1999 IEEE International Conference on Micro Electro Mechanical Systems, Technical Digest, pp. 388-393, 1999.
Hosokawa, Kazuo et al., "Handling of Picoliter Liquid Samples in a Poly(dimethylsiloxane)-Based Microfluidic Device," Analytical Chemistry, vol. 71, No. 20, pp. 4781-4785, Oct. 15, 1999.
Ibrahim et al., "Real-Time Microchip PCR for Detecting Single-Base Differences in Viral and Human DNA," Anal. Chem., vol. 70, pp. 2013-2017, 1998.
Igloi, Gabor L., "Variability in the Stability of DNA-Peptide Nucleic Acid (PNA) Single-Base Mismatched Duplexes: Real-Time Hybridization During Affinity Electrophoresis in PNA-Containing Gels," Proc. Natl. Acad. Sci. USA, vol. 95, pp. 8562-8567, Jul. 1998.
Ikuta, Koji et al., "Three Dimensional Micro Integrated Fluid Systems (MIFS) Fabricated by Stereo Lithography," IEEE, pp. 1-6, 1994.
Ingraham, John L. et al., Growth of the Bacterial Cell, pp. 3 cover pages and 230, 1983.
Jacobson, Ken et al., "International Workshop on the Application of Fluorescence Photobleaching Techniques to Problems in Cell Biology," Federation Proceedings, vol. 42, No. 1, pp. 72-79, Jan. 1983.
Jacobson, Stephen C. et al., "High-Speed Separations on a Microchip," Analytical Chemistry, vol. 66, No. 7, pp. 1114-1118, Apr. 1, 1994.
Jacobson, Stephen C. et al., "Microfluidic Devices for Electrokinetically Driven Parallel and Serial Mixing," Analytical Chemistry, vol. 71, No. 20, pp. 4455-4459, Oct. 15, 1999.
Jacobson, Stephen C. et al., "Open Channel Electrochromatography on a Microchip," Analytical Chemistry, vol. 66, No. 14, pp. 2369-2373, Jul. 15, 1994.
Jannasch, H. W. et al., "Experimental Bacterial Ecology Studied in Continuous Culture," Advances in Microbial Physiology, vol. 11, pp. cover and 165-212, 1974.
Jeffreys, Alec J. et al., "Hypervariable 'Minisatellite' Regions in Human DNA," Nature, vol. 314, pp. 67-73, Mar. 7, 1985.
Jerman, Hal, "Electrically-Activated, Normally-Closed Diaphragm Valves," Transducers '91, 1991 International Conference on Solid-State Sensors and Actuators, pp. cover, 1045-1048, 1991.
Jermutus, Lutz, et al., "Recent Advances in Producing and Selecting Functional Proteins by Using Cell-Free Translation," Current Opinion in Biotechnology, vol. 9, pp. 534-548, 1998.
Jo, Byung-Ho et al., "Fabrication of Three-Dimensional Microfluidic Systems by Stacking Molded Polydimethylsiloxane (PDMS) Layers" SPIE, vol. 3877, pp. 222-229, Sep. 1999.
Jo, Byung-Ho et al., "Three-Dimensional Micro-Channel Fabrication in Polydimethylsiloxane (PDMS) Elastomer," Journal of Microelectromechanical Systems, vol. 9, No. 1, pp. 76-81, Mar. 2000.
Ju, Li-Ya et al., "Application of Silver Staining to the Rapid Typing of the Polymorphism of HLA-DQ Alleles by Enzymatic Amplification and Allele-Specific Restriction Fragment Length Polymorphism," Electrophoresis, vol. 12, pp. 270-273, 1991.
Juárez-Martínez, G. et al., "High-Throughput Screens for Postgenomics: Studies of Protein Crystallization Using Microsystems Technology," Analytical Chemistry, vol. 74, No. 14, pp. 3505-3510, Jul. 15, 2002.
Jung, D. R. et al., "Chemical and Physical Interactions at Metal/Self-Assembled Organic Monolayer Interfaces," pp. 1-54, 1994.
Kagan, C. R., "Organic-Inorganic Hybrid Materials as Semiconducting Channels in Thin-Film Field-Effect Transistors," Science, vol. 286, pp. 945-947, Oct. 29, 1999.
Kamentsky, Louis A. et al., "Spectrophotometer: New Instrument for Ultrarapid Cell Analysis," Science, vol. 150, pp. 630-631, Oct. 29, 1965.

(56) References Cited

OTHER PUBLICATIONS

Kane et al., "Finite element analysis of nonsmooth contact", *Computer Methods in Applied Mechanics and Engineering*, 180(1-2):1-26 (1999).

Kane, R. S. et al., "Patterning Proteins and Cells Using Soft Lithography," Biomaterials, vol. 20, pp. 2363-2376, 1999.

Kanter, Evan et al., "Analysis of Restriction Fragment Length Polymorphisms in Deoxyribonucleic Acid (DNA) Recovered From Dried Bloodstains," Journal of Forensic Sciences, vol. 31, No. 2, pp. 403-408, Apr. 1986.

Kapur, Ravi et al., "Fabrication and Selective Surface Modification of 3-Dimensionally Textured Biomedical Polymers From Etched Silicon Substrates," Journal of Biomedical Materials Research, vol. 33, pp. 205-216, 1996.

Kawano, Yasushi et al., "Rapid Isolation and Identification of Staphylococcal Exoproteins by Reverse Phase Capillary High Performance Liquid Chromatography-Electrospray Ionization Mass Spectrometry," FEMS Microbiology Letters, vol. 189, pp. 103-108, 2000.

Keller, Richard A. et al., "Single-Molecule Fluorescence Analysis in Solution," Applied Spectroscopy, vol. 50, No. 7, pp. 12A-30A, Jul. 1996.

Kenis, Paul J. A. et al., "Microfabrication Inside Capillaries Using Multiphase Laminar Flow Patterning," Science, vol. 285, pp. 83-85, Jul. 2, 1999.

Khandurina et al., "Integrated System for Rapid PCR-Based DNA Analysis in Microfluidic Devices," Anal. Chem., vol. 72, pp. 2995-3000, 2000.

Khoo, Melvin et al., "A Novel Micromachined Magnetic Membrane Microfluid Pump," pp. 1-4, no date.

Xu, Jingdong et al., "Room-Temperature Imprinting Method for Plastic Microchannel Fabrication," Analytical Chemistry, vol. 72, No. 8, pp. 1930-1933, Apr. 15, 2000.

Xu, Xiang et al., "Detection of Programmed Cell Death Using Fluorescence Energy Transfer," Nucleic Acids Research, vol. 26, No. 8, pp. 2034-2035, 1998.

Xue, Qifeng et al., "Integrated Multichannel Microchip Electrospray Ionization Mass Spectrometry: Analysis of Peptides From On-Chip Tryptic Digestion of Melittin," Rapid Communications in Mass Spectrometry, vol. 11, 1253-1256, 1997.

Xue, Qifeng et al., "Multichannel Microchip Electrospray Mass Spectrometry," Analytical Chemistry, vol. 69, No. 3, pp. 426-430, Feb. 1, 1997.

Yang, T. J. et al., "An Apertureless Near-Field Microscope for Fluorescence Imaging," Applied Physics Letters, vol. 76, No. 3, pp. 378-380, Jan. 17, 2000.

Yang, Xing et al., "A Low Power MEMS Silicone/Parylene Valve," Solid-State Sensor and Actuator Workshop, Hilton Head Island, South Carolina, 4 pages, Jun. 7-11, 1998.

Yang, Xing et al., "A MEMS Thermopneumatic Silicone Membrane Valve," IEEE 10th Annual International Workshop of Micro Electro Mechanical Systems, Nagoya, Japan, pp. cover, 114-118, Jan. 26-30, 1997.

Yazdi, Navid et al., "Micromachined Inertial Sensors," Proceedings of IEEE, vol. 86, No. 8, pp. 1640-1659, Aug. 1998.

Yershov, Gennady et al., "DNA Analysis and Diagnostics on Oligonucleotide Microchips," Proc. Natl. Acad. Sci. USA, vol. 93, pp. 4913-4918, May 1996.

Yokobayashi, Yohei et al., "Evolutionary Design of Genetic Circuits and Cell-Cell Communications," Advances in Complex Systems, vol. 6, No. 1, pp. 37-45, 2003.

Young, A. M. et al., "Contoured Elastic-Membrane Microvalves for Microfluidic Network Integration," Journal of Biomechanical Engineering, vol. 121, pp. 2-6, Feb. 1999.

Zaccolo, Manuela et al., "A Genetically Encoded, Fluorescent Indicator for Cyclic AMP in Living Cells," Nature Cell Biology, vol. 2, pp. 25-29, Jan. 2000.

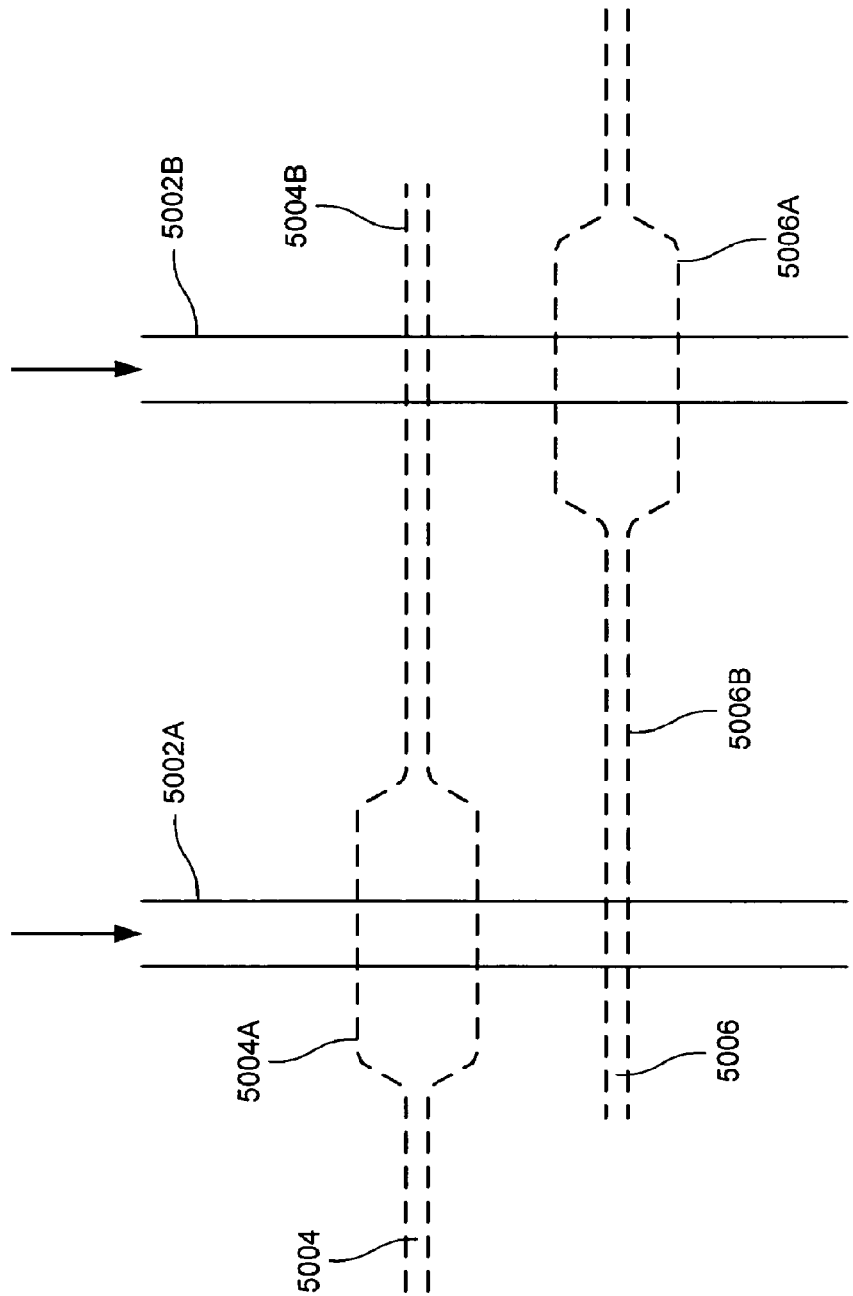

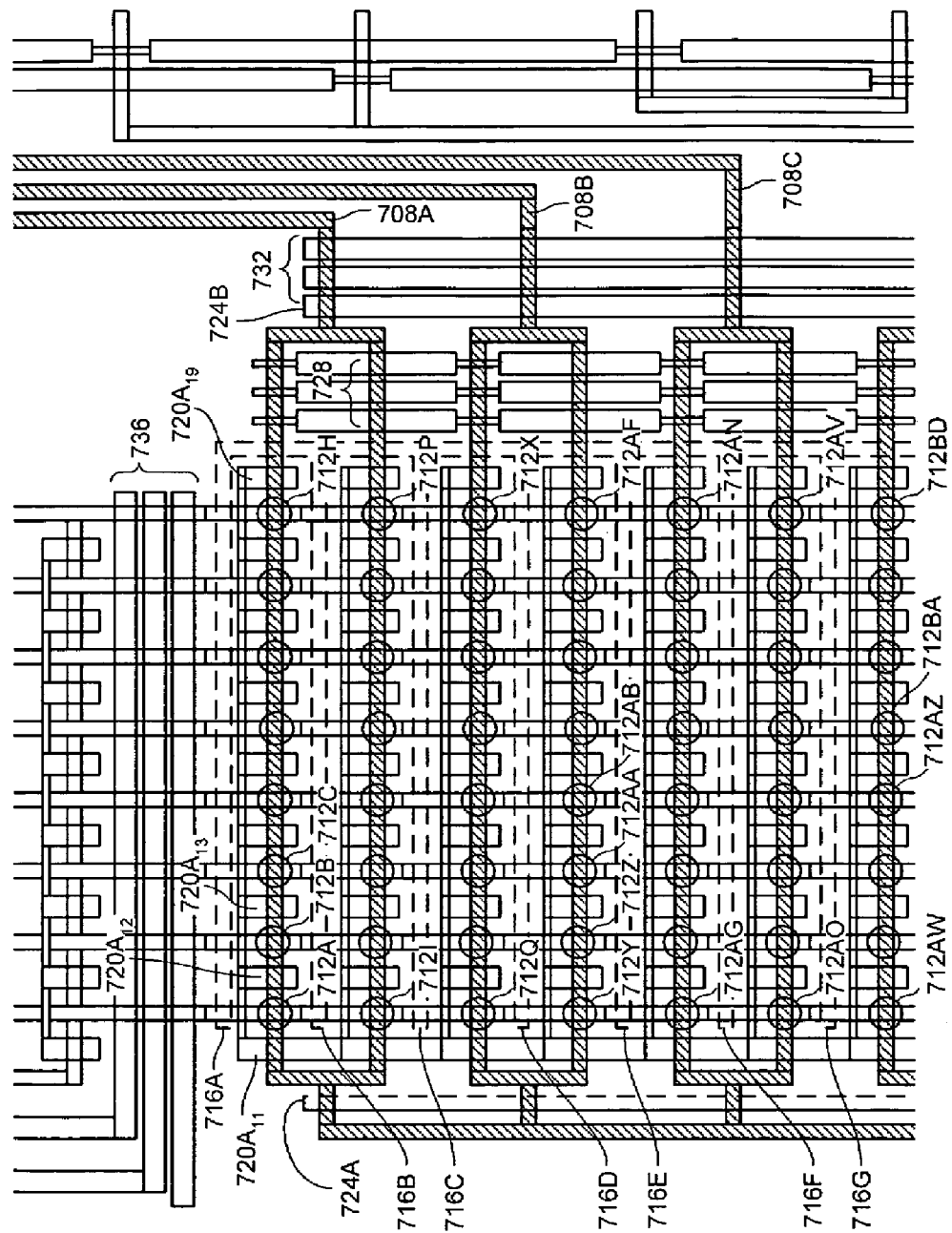

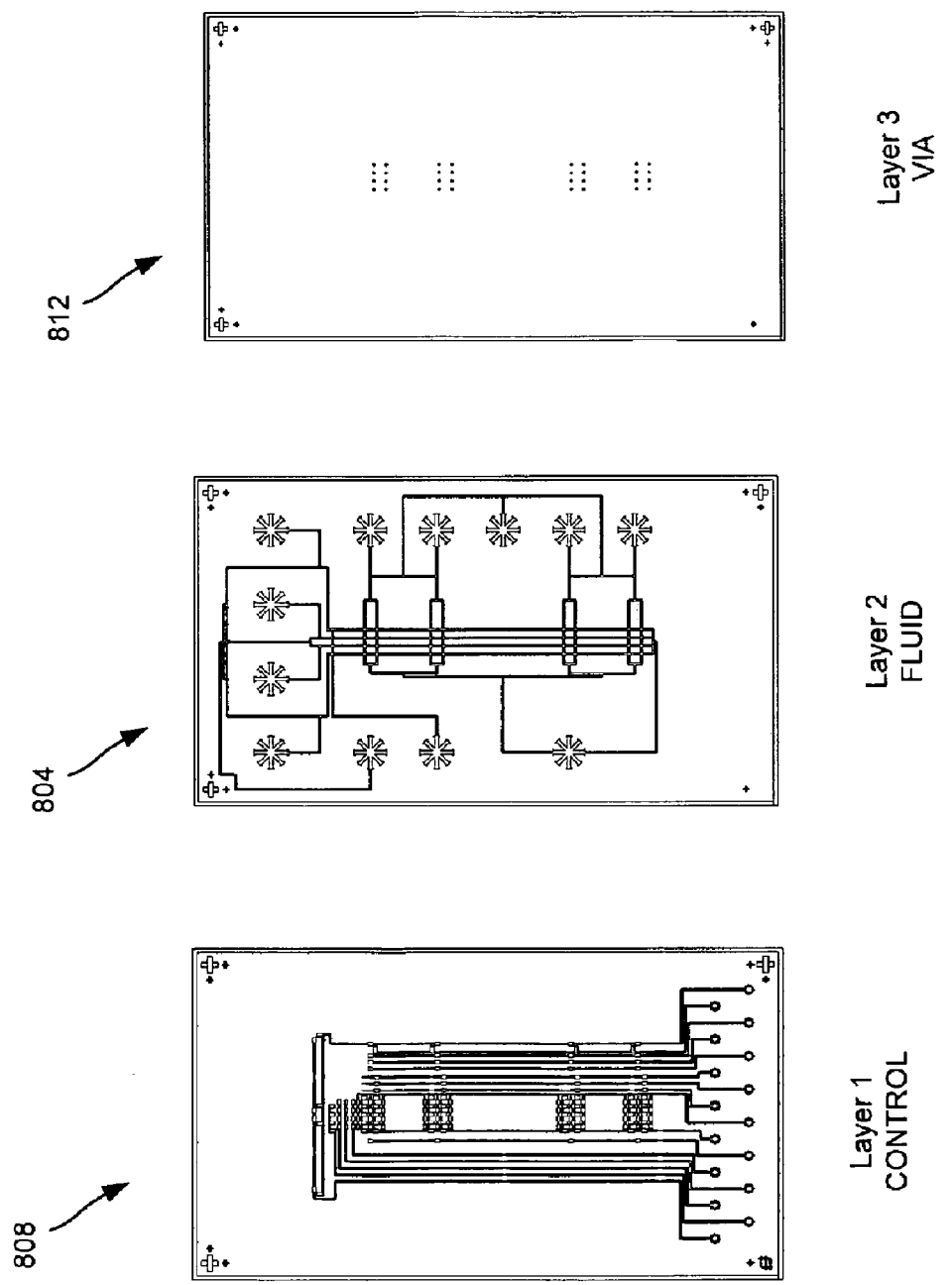

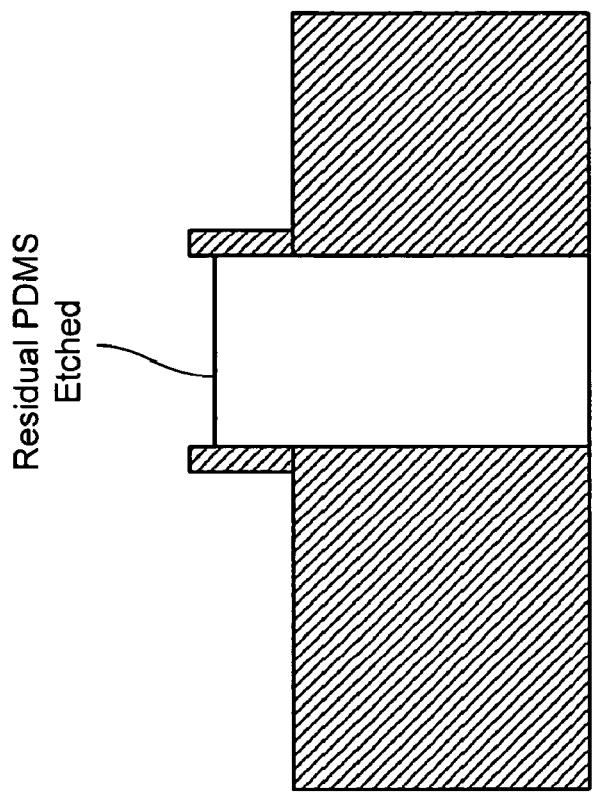
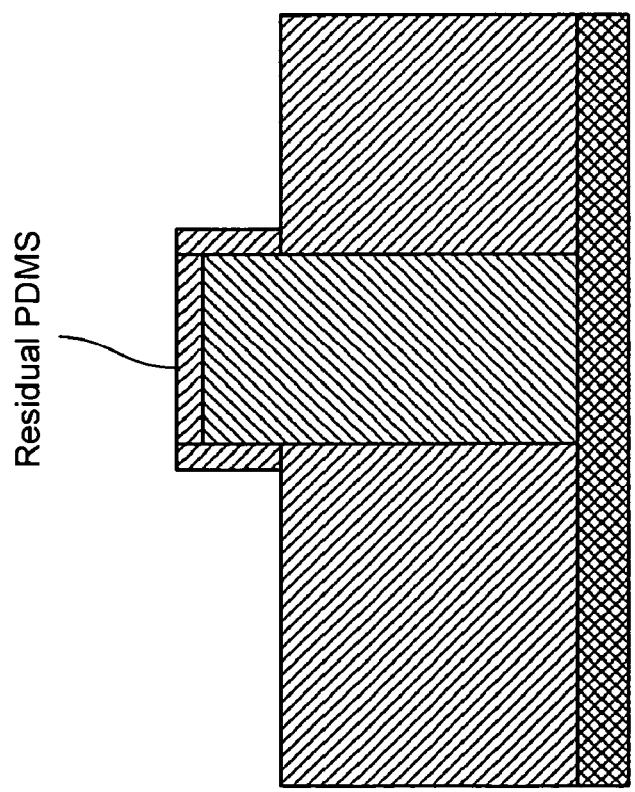
FIG. 9

RECIRCULATING FLUIDIC NETWORK AND METHODS FOR USING THE SAME

CROSS-REFERENCES TO RELATED APPLICATIONS

This application is a continuation of U.S. patent application Ser. No. 13/434,539, filed on Mar. 29, 2012, which is a continuation of U.S. patent application Ser. No. 10/602,489, filed on Jun. 23, 2003, which claims priority to U.S. Provisional Patent Application No. 60/391,292, filed on Jun. 24, 2002. The disclosures of these applications are hereby incorporated by reference in their entirety.

FIELD OF THE INVENTION

The present invention relates to microfluidic apparatus and methods for using the same, such as conducting a variety of assays.

BACKGROUND OF THE INVENTION

There are several goals in the development of biological assays, including utilization of a minimal amount of assay components and sample, simplicity in operation and high throughput capability. Assays preferably require a minimal amount of assay components in order to minimize costs; this becomes a particular issue if certain assay components are expensive and/or a large number of assays are to be conducted. Ideally, assays require only a minimal amount of sample because often only a very limited amount of sample is available. The goal of simplicity of operation often means that the assay is preferably conducted in an integrated format in which all or most aspects of the assay can be conducted with a single device and minimal instrumentation. The goal of high throughput has become increasingly important in view of the trend in current research and drug discovery efforts to screen huge libraries of compounds to identify those that have a desired activity.

Another area where high throughput is particularly important is in proteomics. Proteomics is the study of the complex biological interactions that occur between proteins within a cell. Cells express thousands of proteins at different concentrations. The behavior and interaction of these proteins is dependent upon the cell type, the stage of the cell cycle, and extracellular events, to name a few. Proteins are also chemically modified by cellular machinery, and this modification further differentiates their behavior and interaction with other proteins.

To address some of these problems, particularly the issue of minimizing the amount of sample and assay agents required to conduct an analysis, considerable effort has been invested in the development of microfluidic devices to conduct assays. These devices are characterized by using minute channels for the introduction and transport of the samples and agents necessary to conduct an assay. Unfortunately, current microfluidic devices suffer from a number of shortcomings that limit their usefulness. For example, current microfluidic devices often are manufactured from silicon chips with channels being etched into different silicon layers using established semi-conductor technologies. Such chips, however, are brittle and the stiffness of the material often necessitates high actuation forces. These forces and stresses can cause layers in a multilayer chip to separate from one another. The stiffness of the devices also imposes significant constraints on options for controlling solution flow through the microchannels.

Furthermore, solution flow is controlled at least in part through the use of electrodes to generate electric fields to move molecules and solution via electrophoresis and/or electroosmosis. Reliance on electrodes, however, creates several problems. One problem is that gas is often generated at the electrodes. This can increase pressure within the device potentially causing separation of microfabricated layers. The increased pressure and gas bubbles can also interfere with solution flow through the channels. Additionally, often an elaborate network of electrodes is required in order to achieve the desired level of control over solution transport. Fabrication of such a network can be complicated and increases the expense of the devices. The need for such networks also becomes particularly problematic if a device is to be prepared that includes a large number of channels to facilitate multiplexed and high throughput assay capabilities. Moreover, the use of electrical fields to control solution flow necessarily requires solutions comprising electrolytes (i.e., ionizable compounds). In addition, the use of electric fields can be problematic for applications involving cells as application of the electric fields can negatively affect the cells, often killing them. Consequently, there remains a significant need for improved microfluidic devices, particularly those that are amendable to a wide range of high throughput assay capabilities.

SUMMARY OF THE INVENTION

The present invention provides a variety of microfluidic devices and methods for conducting assays and syntheses. The devices include a solid substrate layer having a surface that is capable of attaching ligand and/or anti-ligand, and an elastomeric layer attached to said solid substrate surface. The elastomeric layer comprises:

(a) a plurality of first flow channels;

(b) a plurality of second flow channels each intersecting and crossing each of said first flow channels thereby providing a plurality of intersecting areas formed at intersections between said first flow channels and said second flow channels, wherein said plurality of first flow channels and said plurality of second flow channels are adapted to allow the flow of a solution therethrough, and wherein said solid substrate surface is in fluid communication with at least said intersecting areas of said plurality of first flow channels and said plurality of second flow channels, and wherein said plurality of first flow channels and/or said plurality of second flow channels are capable of forming a plurality of looped flow channels;

(c) a plurality of control channels;

(d) a plurality of first control valves each operatively disposed with respect to each of said first flow channel to regulate flow of the solution through said first flow channels, wherein each of said first control valves comprises a first control channel and an elastomeric segment that is deflectable into or retractable from said first flow channel upon which said first control valve operates in response to an actuation force applied to said first control channel, the elastomeric segment when positioned in said first flow channel restricting solution flow therethrough;

(e) a plurality of second control valves each operatively disposed with respect to each of said second flow channel to regulate flow of the solution through said second flow channels, wherein each of said second control valves comprises a second control channel and an elastomeric segment that is deflectable into or retractable from said second flow channel upon which said second control valve operates in response to an actuation force applied to said second control channel, the elastomeric segment when positioned in said second flow channel restricting solution flow therethrough;

(f) a plurality of loop forming control valves each operatively disposed with respect to each of said first and/or said second flow channels to form said plurality of looped flow channels, wherein each of said loop forming control valves comprises a loop forming control channel and an elastomeric segment that is deflectable into or retractable from said first and/or said second flow channels upon which said loop forming control valve operates in response to an actuation force applied to said loop forming control channel, the elastomeric segment when positioned in said first and/or said second flow channels restricting solution flow therethrough thereby forming said looped flow channel; and (g) a plurality of recirculating pumps, and wherein each recirculating pump is operatively disposed with respect to one of said looped flow channels such that circulation of solution through each of said looped flow channels can be regulated by one of said recirculating pumps.

Another aspect of the present invention provides a method for conducting a binding assay using the microfluidic devices disclosed herein. The binding assay method generally involves:

applying an actuating force to the second control valves to restrict solution flow through each of the second flow channels;

introducing a reagent comprising a ligand into at least one of the first flow channels under conditions sufficient to attach the ligand to the solid substrate surface;

removing the actuation force to the second flow channel control channel and applying an actuation force to the first control channel such that solution flow through the first flow channel is restricted; and performing a binding assay by introducing a sample solution into the second flow channel under conditions sufficient to specifically bind an antiligand that may be present in the sample solution to the ligand that is covalently attached to the solid substrate surface.

Yet another aspect of the present invention provides a method for producing a microfluidic device comprising a via layer. Such a method generally involves:

producing a control layer, a flow layer, and a via layer from an elastomeric polymer, wherein each of the control layer and the flow layer comprises grooves on its surface for forming control channels and flow channels, respectively;

attaching the control layer to the flow layer such that the grooves in the control layer is attached to a top surface of the flow layer thereby forming a plurality of control channels and attaching the bottom surface of the flow layer to the via layer thereby forming a plurality of first flow channels and a plurality of second flow channels, wherein each first flow channels intersects and crosses each of the second flow channels thereby forming a plurality of channel intersections, and wherein each vias in the via layer is positioned at each channel intersections; and optionally attaching the elastomeric polymer produced in said step (b) to a solid substrate which is comprises a ligand bound to its surface or comprises a functional group which is capable of attaching a ligand.

BRIEF DESCRIPTION OF THE DRAWINGS

In certain drawings, pumps are denoted with a group of three dashed lines and valves denoted by a single dashed line.

FIG. 4 illustrates one arrangement of control and flow channels that allow for selective blockage of certain flow channels.

FIG. 5A is a top schematic of the peristaltic pump. FIG. 5B is a sectional elevation view along line 24B-24B in FIG. 5A.

FIGS. 7A-E depicts an exemplary microfluidic device incorporating various components. FIGS. 7A and 7C show arrangement of each components. FIGS. 7B, 7D and 7E show an isolated close-up view of flow channels and control channels near the intersection of the first and the second flow channels. FIGS. 7D and 7E show different configuration of control channels.

FIGS. 8A-8E show exemplary mold designs for each of the corresponding control layer (808), the fluid (i.e., flow channel) layer (804), and the via layer (812). In FIGS. 8B-D, an alignment mask 816 is also shown.

FIG. 9 illustrates formation of a via layer and etching step to open the vias where residual PDMS exist on the mold during the fabrication step.

FIG. 10B shows one particular microfluidic device design having an integrated fluid layer and control layer.

DETAILED DESCRIPTION OF SPECIFIC EMBODIMENTS

I. Definitions

Figure 1A:
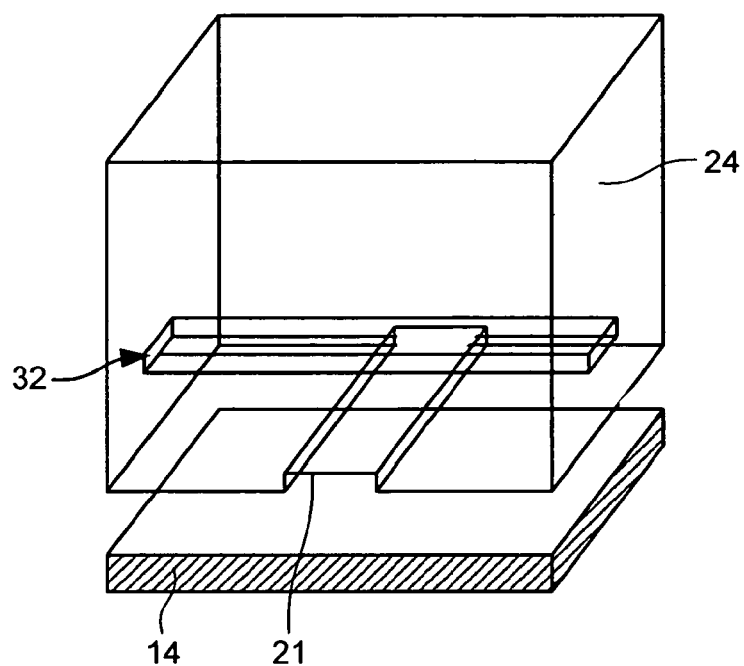
FIGS. 1A and 1B are illustrations of an elastomeric block and the arrangement of a control and flow channel therein.

Unless defined otherwise, all technical and scientific terms used herein have the meaning commonly understood by a person skilled in the art to which this invention belongs. The following references provide one of skill with a general definition of many of the terms used in this invention: Singleton et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); THE GLOSSARY OF GENETICS, 5TH ED., R. Rieger et al. (eds.), Springer Verlag (1991); and Hale & Marham, THE HARPER COLLINS DICTIONARY OF BIOLOGY (1991). As used herein, the following terms have the meanings ascribed to them unless specified otherwise.

The term "elastomer" and "elastomeric" has its general meaning as used in the art. Thus, for example, Allcock et al. (Contemporary Polymer Chemistry, 2nd Ed.) describes elastomers in general as polymers existing at a temperature between their glass transition temperature and liquefaction temperature. Elastomeric materials exhibit elastic properties because the polymer chains readily undergo torsional motion to permit uncoiling of the backbone chains in response to a force, with the backbone chains recoiling to assume the prior shape in the absence of the force. In general, elastomers deform when force is applied, but then return to their original shape when the force is removed. The elasticity exhibited by elastomeric materials can be characterized by a Young's modulus. The elastomeric materials utilized in the microfluidic devices disclosed herein typically have a Young's modulus of between about 1 Pa-1 TPa, in other instances between about 10 Pa-100 GPa, in still other instances between about 20 Pa-1 GPa, in yet other instances between about 50 Pa-10 MPa, and in certain instances between about 100 Pa-1 MPa. Elastomeric materials having a Young's modulus outside of these ranges can also be utilized depending upon the needs of a particular application.

Some of the microfluidic devices described herein are fabricated from an elastomeric polymer such as GE RTV 615 (formulation), a vinyl-silane crosslinked (type) silicone elastomer (family). However, the present microfluidic systems are not limited to this one formulation, type or even this family of polymer; rather, nearly any elastomeric polymer is suitable. Given the tremendous diversity of polymer chemistries, precursors, synthetic methods, reaction conditions, and potential additives, there are a large number of possible elastomer systems that can be used to make monolithic elastomeric microvalves and pumps. The choice of materials typically depends upon the particular material properties (e.g., solvent resistance, stiffness, gas permeability, and/or temperature stability) required for the application being conducted. Additional details regarding the type of elastomeric materials that can be used in the manufacture of the components of the microfluidic devices disclosed herein are set forth in U.S. application Ser. No. 09/605,520, filed Jun. 27, 2000, U.S. application Ser. No. 09/724,784, filed Nov. 28, 2000, and PCT publication WO 01/01025, all of which are incorporated herein by reference in their entirety.

"Ligand" generally refers to any molecule that binds to an antiligand to form a ligand/antiligand pair. Thus, a ligand is any molecule for which there exists another molecule (i.e., the antiligand) that specifically or non-specifically binds to the ligand, owing to recognition of some portion or feature of the ligand.

"Antiligand" is a molecule that specifically or nonspecifically interacts with another molecule (i.e., the ligand).

Exemplary ligand/antiligand pairs include antibody/antigen, enzyme/substrate, oligonucleotide/complementary oligonucleotide, nucleic acid/probe, drug molecule/cellular protein, drug molecule/cell membrane, cellular protein/cellular protein, protein affinity tag/protein, protein affinity tag/metal ion, Protein A or G/antibody, as well as other ligand/antiligand pairs that form a corresponding complex. It should be appreciated that the terms ligand and antiligand for a given ligand/antiligand pair is interchangeable. Thus, for example, either of the antibody or antigen can be considered to be a ligand as long as the other pair is considered to be the antiligand.

"Polypeptide," "peptides" and "protein" are used interchangeably herein and include a molecular chain of amino acids linked through peptide bonds. The terms do not refer to a specific length of the product. The terms include post-translational modifications of the polypeptide, for example, glycosylations, acetylations, phosphorylations and the like, and also can include polypeptides that include amino acid analogs and modified peptide backbones.

The term "antibody" as used herein includes antibodies obtained from both polyclonal and monoclonal preparations, as well as the following: (i) hybrid (chimeric) antibody molecules (see, for example, Winter et al. (1991) Nature 349:293-299; and U.S. Pat. No. 4,816,567); (ii) F(ab')2 and F(ab) fragments; (iii) Fv molecules (noncovalent heterodimers, see, for example, Inbar et al. (1972) Proc. Natl. Acad. Sci. USA 69:2659-2662; and Ehrlich et al. (1980) Biochem 19:4091-4096); (iv) single-chain Fv molecules (sFv) (see, for example, Huston et al. (1988) Proc. Natl. Acad. Sci. USA 85:5879-5883); (v) dimeric and trimeric antibody fragment constructs; (vi) humanized antibody molecules (see, for example, Riechmann et al. (1988) Nature 332:323-327; Verhoeyan et al. (1988) Science 239:1534-1536; and U.K. Patent Publication No. GB 2,276,169, published 21 Sep. 1994); (vii) Mini-antibodies or minibodies (i.e., sFv polypeptide chains that include oligomerization domains at their C-termini, separated from the sFv by a hinge region; see, e.g., Pack et al. (1992) Biochem 31:1579-1584; Cumber et al. (1992) J. Immunology 149B:120-126); and, (vii) any functional fragments obtained from such molecules, wherein such fragments retain specific-binding properties of the parent antibody molecule.

The terms "nucleic acid," "polynucleotide," and "oligonucleotide" are used herein to include a polymeric form of nucleotides of any length, including, but not limited to, ribonucleotides or deoxyribonucleotides. There is no intended distinction in length between these terms. Further, these terms refer only to the primary structure of the molecule. Thus, in certain embodiments these terms can include triple-, double- and single-stranded DNA, as well as triple-, double- and single-stranded RNA. They also include modifications, such as by methylation and/or by capping, and unmodified forms of the polynucleotide. More particularly, the terms "nucleic acid," "polynucleotide," and "oligonucleotide," include polydeoxyribonucleotides (containing 2-deoxy-D-ribose), polyribonucleotides (containing D-ribose), any other type of polynucleotide which is an N- or C-glycoside of a purine or pyrimidine base, and other polymers containing nonnucleotidic backbones, for example, polyamide (e.g., peptide nucleic acids (PNAs)) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA.

A "probe" is an nucleic acid capable of binding to a target nucleic acid of complementary sequence through one or more types of chemical bonds, usually through complementary base pairing, usually through hydrogen bond formation, thus forming a duplex structure. The probe binds or hybridizes to a "probe binding site." The probe can be labeled with a detectable label to permit facile detection of the probe, particularly once the probe has hybridized to its complementary target. The label attached to the probe can include any of a variety of different labels known in the art that can be detected by chemical or physical means, for example. Suitable labels that can be attached to probes include, but are not limited to, radioisotopes, fluorophores, chromophores, mass labels, electron dense particles, magnetic particles, spin labels, molecules that emit chemiluminescence, electrochemically active molecules, enzymes, cofactors, and enzyme substrates. Probes can vary significantly in size. Some probes are relatively short. Generally, probes are at least 7 to 15 nucleotides in length. Other probes are at least 20, 30 or 40 nucleotides long. Still other probes are somewhat longer, being at least 50, 60, 70, 80, 90 nucleotides long. Yet other probes are longer still, and are at least 100, 150, 200 or more nucleotides long. Probes can be of any specific length that falls within the foregoing ranges as well.

The term "complementary" means that one nucleic acid is identical to, or hybridizes selectively to, another nucleic acid molecule. Selectivity of hybridization exists when hybridization occurs that is more selective than total lack of specificity. Typically, selective hybridization will occur when there is at least about 55% identity over a stretch of at least 14-25 nucleotides, preferably at least 65%, more preferably at least 75%, and most preferably at least 90%. Preferably, one nucleic acid hybridizes specifically to the other nucleic acid. See M. Kanehisa, *Nucleic Acids Res.* 12:203 (1984).

The term "stringent conditions" refers to conditions under which a probe or primer will hybridize to its target subsequence, but to no other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. In other instances, stringent conditions are chosen to be about 20° C. or 25° C. below the melting temperature of the sequence and a probe with exact or nearly exact complementarity to the target. As used herein, the melting temperature is the temperature at which a population of double-stranded nucleic acid molecules becomes half-dissociated into single strands. Methods for calculating the $T_m$ of nucleic acids are well known in the art (see, e.g., Berger and Kimmel (1987) Methods in Enzymology, vol. 152: Guide to Molecular Cloning Techniques, San Diego: Academic Press, Inc. and Sambrook et al. (1989) Molecular Cloning: A Laboratory Manual, 2nd ed., vols. 1-3, Cold Spring Harbor Laboratory), both incorporated herein by reference. As indicated by standard references, a simple estimate of the $T_m$ value can be calculated by the equation: $T_m=81.5+0.41(\% \text{ G+C})$, when a nucleic acid is in aqueous solution at 1 M NaCl (see e.g., Anderson and Young, "Quantitative Filter Hybridization," in *Nucleic Acid Hybridization* (1985)). Other references include more sophisticated computations which take structural as well as sequence characteristics into account for the calculation of $T_m$. The melting temperature of a hybrid (and thus the conditions for stringent hybridization) is affected by various factors such as the length and nature (DNA, RNA, base composition) of the probe and nature of the target (DNA, RNA, base composition, present in solution or immobilized, and the like), and the concentration of salts and other components (e.g., the presence or absence of formamide, dextran sulfate, polyethylene glycol). The effects of these factors are well known and are discussed in standard references in the art, see e.g., Sambrook, supra, and Ausubel, supra. Typically, stringent conditions will be those in which the salt concentration is less than about 1.0 M Na ion, typically about 0.01 to 1.0 M Na ion concentration (or other salts) at pH 7.0 to 8.3 and the temperature is at least about 30° C. for short probes or primers (e.g., 10 to 50 nucleotides) and at least about 60° C. for long probes or primers (e.g., greater than 50 nucleotides). Stringent conditions can also be achieved with the addition of destabilizing agents such as formamide.

A "small molecule" means a synthetic molecule having a molecular weight of less than 1000 daltons, more typically 500 daltons or less. Such molecules include, for example, monosaccharides, polysaccharides, polypeptides, sterols, amino acids, lipids and nucleic acids.

The phrase "specifically binds" generally refers to binding of a ligand and an antiligand, or vice versa, with greater affinity and specificity than to other components in the sample. Thus, the term refers to a binding reaction which is determinative of the presence of the ligand in the presence of a heterogeneous population of other biological compounds. Thus, under designated conditions, a specified ligand binds preferentially to a particular antiligand and does not bind in a significant amount to other molecules present in the sample. Typically, a molecule or ligand (e.g., an antibody) that specifically binds to an antiligand has an association constant of at least $10^3$ $M^{-1}$ or $10^4$ $M^{-1}$, sometimes $10^5$ $M^{-1}$ or $10^6$ $M^{-1}$, in other instances $10^6$ $M^{-1}$ or $10^7$ $M^{-1}$, preferably $10^8$ $M^{-1}$ to $10^9$ $M^{-1}$, and more preferably, about $10^{10}$ $M^{-1}$ to $10^{11}$ $M^{-1}$ or higher.

A difference is typically considered to be "statistically significant" if the difference is greater than the level of experimental error. More specifically, a difference is statistically significant if the probability of the observed difference occurring by chance (the p-value) is less than some predetermined level. As used herein a "statistically significant difference" refers to a p-value that is <0.05, preferably <0.01 and most preferably <0.001.

The term "label" refers to a molecule or an aspect of a molecule that can be detected by physical, chemical, electromagnetic and other related analytical techniques. Examples of detectable labels that can be utilized include, but are not limited to, radioisotopes, fluorophores, chromophores, mass labels, electron dense particles, magnetic particles, spin labels, molecules that emit chemiluminescence, electrochemically active molecules, enzymes, cofactors, and enzyme substrates. The term "detectably labeled" means that an agent has been conjugated with a label or that an agent has some inherent characteristic (e.g., size, shape or color) that allows it to be detected without having to be conjugated to a separate label.

II. Introduction

Described herein are microfluidic devices and methods for conducting a variety of different assays, such as high throughput screening assays, cellular assays or assays involving cellular components, and syntheses, such as combinatorial syntheses. The microfluidic devices are characterized in part by including various components such as flow channels, control channels, valves and/or pumps, at least some of which are manufactured from elastomeric materials.

In addition, microfluidic devices of the present invention comprise a solid substrate layer. The solid substrate layer comprises a surface to which one or more ligands are attached. Alternatively, the solid substrate surface comprises a functional group or is capable of being derivatized such that a ligand can be attached to its surface. Preferably, the ligand is covalently attached to the solid substrate surface.

The presence of a ligand on the solid substrate surface allows a variety of assays as described in detail below.

The microfluidic devices of the present invention include a plurality of first flow channels and a plurality of a second flow channels. The presence of more than one flow channels allows parallel assay on a single microfluidic device thereby increasing the throughput. Each of the first flow channels intersects and crosses each of the second flow channels resulting in a plurality of intersecting areas. By introducing a fluid comprising a ligand in the first flow channel and introducing a fluid which may comprise an antiligand in the second flow channel, the binding assay are achieved on the intersecting areas of the first and the second flow channels.

By selectively activating appropriate valves, at least one of the plurality of first flow channels or the plurality of second flow channels are capable of forming a plurality of looped flow channel. The valves comprise a control channel separated from a flow channel by an elastomeric segment or membrane that can be deflected into or withdrawn from the flow channel upon actuation of the control channel (e.g., by applying pressure or a vacuum to the control channel). When the elastomeric segment extends into the flow channel, it blocks solution flow through the channel. Each of the looped flow channels can also comprise a pump thereby providing a means for circulating or recirculating the solution within the looped flow channel. The pump can comprise one or more control valves, preferably more than one control valves, and more preferably three control valves that can be actuated in a desired sequence.

In addition, microfluidic devices of the present invention comprise a plurality of first control valves and a plurality of second control valves. The each of the first control valves regulates the flow of a solution through each of the first flow channels and each of the second control valves regulates the flow of a solution through each of the second flow channels. In this manner, selective activation of control valves prevents the flow of solution to undesired flow channels.

Some microfluidic devices of the present invention also comprise a plurality of holding valves each forming a holding space that encapsulates one intersecting area of the first and the second flow channels. In this manner, the fluid flow within the intersecting areas can be restricted thereby providing a means for contacting the solution to the intersecting areas for a prolonged period. The holding valve comprises two pairs of valves, one pair in the first flow channel and another pair in the second flow channel. In each pair of valves, the valves are positioned relative to one another such that they are positioned in the different side of the intersecting area. Thus, when the elastomeric segment of the holding valves extend into the flow channel, the elastomeric segment form a holding space within the flow channel that is bounded by the extended elastomeric segment and encapsulating and isolating each individual intersecting areas. In one embodiment, the holding valves are formed from a combination of both the plurality of first control valves and the plurality of second control valves forms a plurality of holding valves.

Microfluidic devices of the present invention can also include a variety of pumps, such as a pump for transporting a fluid along the first flow channels and a pump for transporting a fluid along the second flow channels. Certain pumps are characterized by including a plurality, preferably at least three, control channels that are separated from the flow channel by an elastomeric segment that can be deflected into the flow channel when actuated. By actuating the control channels in a staggered fashion, a peristaltic effect can be induced.

In addition, microfluidic devices of the present invention can also include optional reservoirs or storage areas (i.e., fluid chambers). Such reservoirs or chambers are typically positioned at or near the inlet portion of the flow channels to provide a storage site for fluids prior to introducing the fluid into the first or the second flow channels. Each flow channel can have its own reservoir, or two or more flow channels can have one common reservoir. Similarly, microfluidic devices of the present invention can also include optional waste reservoirs for collecting fluids from the flow channel outlets or the waste flow channel.

Furthermore, microfluidic devices of the present invention can also include a waste flow channel and/or waste collection chamber. Typically, all the outlets of the first flow channels are in fluid communication with the first waste flow channel thereby eliminating a need for a multiple waste flow channels for the first flow channels. Similarly, all the outlets of the second flow channels are in fluid communication with the second waste flow channel thereby eliminating a need for a multiple waste flow channels for the second flow channels. However, it should be appreciated that the present invention is not limited to having a single waste channel for each of the first and the second flow channels.

The flow channels are formed within the elastomeric layer with at least a portion of the flow channel being enclosed by the solid substrate. In one embodiment, the solid substrate forms one wall of the flow channel, i.e., the flow channels is located within the interface of the solid substrate and the elastomeric layer. In another embodiment, the entire flow channel is formed within the elastomeric layer except for the intersecting areas of the first and the second flow channels where the solid substrate forms one side of the wall of the flow channel.

The microfluidic devices provided herein can be utilized in a number of different assay applications, for example, high throughput ligand/antiligand binding assays. By controllably introducing different solutions into the different flow channels, a number of different analyses or syntheses can be performed at the same time. Thus, the microfluidic devices can be used to conduct a number of different types of assays.

The devices disclosed herein can be utilized to screen individual compounds and libraries of compounds to identify those having a desired effect in various in vitro model systems. For example, assays utilizing the microfluidic devices provided herein can be utilized to screen libraries of compounds for those capable of fully or partially inhibiting reactions or processes that have undesirable consequences. For instance, libraries can be screened to identify compounds that inhibit reactions or processes involved in the onset of disease or particular symptoms associated with the disease (e.g., bacterial and viral infections, hereditary diseases and cancer). Alternatively, individual compounds and libraries of compounds can be screened to identify particular compounds that activate or promote reactions or processes of interest. Compounds showing activity in initial screening can then be subjected to other screens or modified and rescreened to identify compounds suitable for formulation as pharmaceutical agents in treating the disease or symptoms associated with the disease under investigation.

The devices disclosed herein can also be utilized to identify the concentrations of various proteins or proteins with post-translational modifications, such as glycosylation or phosphorylation. For example, assays utilizing the microfluidic devices provided herein can be utilized to screen cell populations or cell types for variations in protein concentrations. Such information can be useful in determining phenotypes associated with bacterial and viral infections, hereditary diseases and cancer, for example. Such information can be useful in identifying new pharmaceutical drug targets or for elucidating the significance of various cellular proteins.

In general such screening methods involve attaching a ligand (e.g., cell, enzyme, oligonucleotide, peptide, or antibody, etc.) to the solid substrate surface within the flow channel, introducing an antiligand (e.g., small molecule, substrate, complimentary oligonucleotide, binding peptide, or antigen, etc., respectively) and measuring the binding activity. The antiligand can be labeled to further assist in detecting ligand/antiligand binding. Alternatively, a labeled ligand can be added to form ligand/antiligand/labeled ligand triple complex. In this manner, ELISA (enzyme-linked immuno) and FLISA (fluorescence-linked) assays and other conventionally known ligand/antiligand/labeled ligand triple complex assays can be achieved.

Typically, the ligand is attached to the solid substrate surface by introducing appropriate reagents into the microfluidic device through the first flow channels. After the ligand is attached, the unbound ligands and reagents are removed, e.g., by washing the first flow channels with a washing solution. Alternatively, when only the channel intersecting areas are of interest, the unbound ligands can be removed by closing the first control valve and introducing the washing solution through the second flow channels. A sample solution which may comprising an antiligand is then introduced through the second flow channels. The sample solution can be circulated through the second flow channels to afford prolonged exposure to the bound ligand or the sample solution can be continuously flowed through the second flow channel. Still alternatively, the sample solution can be held within the holding space to allow prolonged contact with the bound ligand. When a triple complex assay is performed, the unbound ligand is removed from the second flow channels, e.g. by flushing the second flow channels with a washing solvent. Again, when only the channel intersecting areas are of interest, the unbound ligands can be removed by closing the second control valve and introducing the washing solution through the first flow channels. A ligand solution, in which the ligand is optionally labeled, is then introduced into the first or the second flow channels. In this manner, the binding assay occurs at only the intersecting areas.

One can determine the binding assay by removing the elastomeric layer from the solid substrate layer and measuring the appropriate binding parameter(s) at the intersecting areas. Alternately, the binding assay can be determined with the elastomeric layer still in contact with the solid substrate.

Similarly, the valves and pumps of the microfluidic devices can be utilized to controllably react different reactants in the different intersecting areas to perform combinatorial syntheses.

III. Microfluidic Elements

A number of elements that are commonly utilized in the microfluidic devices disclosed herein are described below. It should be recognized that these elements can be considered modules that can be combined in different ways to yield an essentially unlimited number of configurations. Further, using the following elements or modules one can tailor the microfluidic device to include those elements useful for the particular application(s) to be conducted with the device.

A. General

It is to be understood that the present invention is not limited to fabrication of microfluidic devices in the manner discussed below. Rather, other suitable methods of fabricating the present microfluidic devices, including modifying the present methods, are also within the scope of the present invention.

The microfluidic devices disclosed herein are typically constructed by single and multilayer soft lithography (MLSL) techniques and/or sacrificial-layer encapsulation methods. Both of these methods are described in detail by Unger et al. (2000) Science 288:113-116, in U.S. patent application Ser. No. 09/605,520, filed Jun. 27, 2000, in U.S. patent application Ser. No. 09/724,784, filed Nov. 28, 2000, and in PCT publication WO 01/01025, all of which are incorporated herein in their entirety. The microfluidic devices provided herein can include a variety of different components that are described in detail infra. These components can be arranged in a large number of different configurations depending upon the particular application.

The following sections describe the general components that are utilized in the devices; these sections are followed with exemplary configurations that can be utilized in various types of assays and high throughput screening.

As described in detail below, the elastomeric layer portion of the flow channels can be tailored to the particular application by modifying the internal surfaces of the elastomeric layer flow channels.

B. Solid Substrate

The microfluidic devices of the present invention allow conducting assay on the solid substrate. Therefore, any material which can be derivatized to allow attachment of a ligand, or a linker molecule, can be used as the solid substrate. Exemplary materials suitable for the solid substrate of the present invention include, but are not limited to, glass (including controlled-pore glass), polystyrene, polystyrene-divinylbenzene copolymer (e.g., for synthesis of peptides), silicone rubber, quartz, latex, polyurethane, gold and other derivatizable transition metals, silicon dioxide, silicon nitride, gallium arsenide, and the like. Solid substrate materials are preferably resistant to the variety of undesired chemical reaction conditions to which they may be subjected.

Individual planar solid substrate can have varied dimensions from which a plurality of individual arrays or chips may be fabricated. The term "array" or "chip" is used to refer to the final product of the individual array of ligand/antiligand complex, having a plurality of different positionally distinct ligand/antiligand complex coupled to the surface of the solid substrate. The size of a solid substrate is generally defined by the number and nature of arrays that will be produced from the solid substrate. For example, more complex arrays will generally utilize larger areas and thus employ larger solid substrate, whereas simpler arrays may employ smaller surface areas, and thus, smaller solid substrate.

The size of solid substrate generally depends on the number of ligand/antiligand complex arrays desired. Typically, however, the solid substrate dimensions can be anywhere from about 1 cm×1 cm to about 30 cm×30 cm. In one particular embodiment of the present invention, the solid substrate is a standard 1"×3" or 2"×3" glass microscope slides, or 1"×1", 1.5"×1.5", or 2"×2" quartz glass windows.

Stripping and Rinsing

In order to ensure maximum efficiency in attaching a ligand to its surface, it is generally desirable to provide a clean solid substrate surface upon which the ligand attaching reactions are to take place. Accordingly, in some embodiments of the present invention, the solid substrate is stripped to remove any residual dirt, oils or other materials which may interfere with attachment of ligands.

The process of stripping the solid substrate typically involves applying, immersing or otherwise contacting the solid substrate with a stripping solution. Stripping solutions may be selected from a number of commercially available, or readily prepared chemical solutions used for the removal of dirt and oils, which solutions are well known in the art. Particularly preferred stripping solutions are composed of a mixture of concentrated $H_2O_2$ and $NH_4OH$. Gas phase cleaning and preparation methods may also be applied to the solid substrate using techniques that are well known in the art.

Derivatization

While not necessary, after the solid substrate surface has been cleaned and stripped, the surface may be derivatized to provide other sites or functional groups on the solid substrate surface for attaching ligands. In particular, derivatization provides reactive functional groups, e.g., hydroxyl, carboxyl, amino groups or the like, to which the ligand or a linker can be attached. For example, the solid substrate surface can be derivatized using silane in either water or ethanol. Preferred silanes include mono- and dihydroxy-alkylsilanes, which provide a hydroxyl functional group on the surface of the substrate. Alternatively, aminoalkyltri-alkoxysilanes can be used to provide the initial surface modification with a reactive amine functional group. Particularly preferred are 3-aminopropyltriethoxysilane and 3-aminopropyltrimethoxysilane ("APS"). Derivatization of the substrate using these latter amino silanes provides a linkage that is stable under various assaying conditions and other chemical reaction conditions (for oligonucleotide synthesis, this linkage is typically a phosphoramidite linkage, as compared to the phosphodiester linkage where hydroxyalkylsilanes are used). Additionally, this amino silane derivatization provides several advantages over derivatization with hydroxyalkylsilanes. For example, the aminoalkyltrialkoxysilanes are inexpensive and can be obtained commercially in high purity from a variety of sources, the resulting primary and secondary amine functional groups are more reactive nucleophiles than hydroxyl groups; thus, providing a reactive site for attaching ligands. In addition, the aminoalkyltrialkoxysilanes are less prone to polymerization during storage, and they are sufficiently volatile to allow application in a gas phase in a controlled vapor deposition process. Other suitable linkers are well known to one of ordinary skill in the art.

Additionally, silanes can be prepared having protected or "masked" hydroxyl groups and which possess significant volatility. As such, these silanes can be readily purified, e.g., by distillation, and can be readily employed in gas-phase deposition methods of silanating solid support surfaces. After coating these silanes onto the surface of the solid substrate, the hydroxyl groups may be deprotected with a brief chemical treatment, e.g., dilute acid or base, which will not attack the solid substrate-silane bond, so that the solid substrate can then be used for attaching ligands or polymer synthesis. Examples of such silanes include acetoxyalkylsilanes, such as acetoxyethyltrichlorosilane, acetoxypropyl-trimethoxysilane, which may be deprotected after application, e.g., using vapor phase ammonia and methylamine or liquid phase aqueous or ethanolic ammonia and alkylamines The physical operation of silanation of the solid substrate generally involves dipping or otherwise immersing the solid substrate in the silane solution. Following immersion, the solid substrate is generally spun laterally to provide a uniform distribution of the silane solution across the surface of the solid substrate. This ensures a more even distribution of reactive functional groups on the surface of the solid substrate. Following application of the silane layer, the silanated solid substrate may be baked to polymerize the silanes on the surface of the solid substrate and improve the reaction between the silane reagent and the solid substrate surface.

Alternatively, the silane solution may be contacted with the surface of the solid substrate using controlled vapor deposition methods or spray methods. These methods involve the volatilization or atomization of the silane solution into a gas phase or spray, followed by deposition of the gas phase or spray upon the surface of the solid substrate, usually by ambient exposure of the surface of the solid substrate to the gas phase or spray. Vapor deposition typically results in a more even application of the derivatization solution than simply immersing the solid substrate into the solution.

The efficacy of the derivatization process, e.g., the density and uniformity of functional groups on the solid substrate surface, may generally be assessed by adding a fluorophore which binds the reactive groups, e.g., a fluorescent phosphoramidite such as Fluoreprime® from Pharmacia, Corp., Fluoredite® from Millipore, Corp. or FAM® from ABI, and looking at the relative fluorescence across the surface of the solid support.

As described above, ligands can be attached to the solid substrate surface prior to attaching the elastomeric layer to the solid substrate surface. Alternatively, ligands can be attached to the solid substrate surface after attaching the elastomeric layer to the solid substrate. Such ligand attachment can be achieved by introducing an appropriate reagent solution into the flow channel under conditions sufficient to allow bond formation between the solid substrate surface and the ligand.

C. Channels

The channels through which fluid is transported in the microfluidic devices are typically formed at least in part from elastomeric layer. Separated from the flow channels by an elastomeric membrane are control channels which can be actuated to control or regulate fluid (e.g., solution) flow through the flow channels. As described in greater detail below in the section on valves, actuation of the control channel (e.g., pressurization or pressure reduction within the flow channel) causes the elastomeric segment separating the flow and control channel to be extended into the flow channel, thus forming a valve that blocks solution flow in the flow channel. Typically, the flow and control channels cross one another at an angle.

The flow and control channels can be manufactured from two primary techniques. One approach is to cast a series of elastomeric layers on a micro-machined mold and then fuse the layers together. The second primary method is to form patterns of photoresist on an elastomeric layer in a desired configuration; in particular, photoresist is deposited wherever a channel is desired. These two different methods of forming the desired configuration of flow and control channels, as well as other details regarding channel dimensions and shape, are described in considerable detail in PCT publication WO 01/01025, U.S. application Ser. No. 09/605, 520, filed Jun. 27, 2000, U.S. application Ser. No. 09/724, 784, filed Nov. 28, 2000, and by Unger et al. (2000) Science 288:113-116, each of which is incorporated herein by reference in its entirety.

C. Sample Inputs

There are a number of different options for introducing a solution into a flow channel. One option is to simply inject solution into a flow channel using a needle, for example. One can also pressurize a container of solution to force solution from the container into a flow channel. A related approach involves reducing pressure at one end of a flow channel to pull solution into a distal opening in the flow channel.

Individual input/inlet lines can be formed that can be loaded manually using single channel micropipettors. The microfluidic devices can be sized according to industry size-specifications (e.g., footprint is 127.76 0.12×85.47 0.12 mm) for plate readers and robotics and are designed to interface with generic multichannel robotic pipettors/samplers with standardized interwell spacings (pitch). Dimensional standards for these types of plate/devices are described at http://www.torntec.com/Pages/platstan.html and http://www.sbsonline.com. Custom micropipettors that do not conform to this standard can also be utilized. In some systems, an electropipettor that is in fluid communication with a sample input channel is utilized. Micropipettors of this type are described, for example, in U.S. Pat. No. 6,150,180.

Inlets to the microfluidic devices disclosed herein can be holes or apertures that are punched, drilled or molded into the elastomeric matrix. Such apertures are sometimes referred to as "vias." The vias can also be formed using photoresist techniques. For example, metal etch blocking layers used in combination with patterning of photoresist masks and the use of solvents to remove etch blocking layers can be utilized to create vias. Vertical vias between channels in successive elastomer layers can be formed utilizing negative mask techniques. Vias can also be formed by ablation of elastomer material through application of an applied laser beam. All of these techniques are described in greater detail in U.S. application Ser. No. 09/605,520.

Inlets can optionally be lined with couplings (e.g., made of Teflon) to provide a seal with the pipette tips or syringe tip used to inject a solution.

As described further below, pumps formed from elastomeric materials can be used to transport solution through the flow channels. For channels of known dimensions, one can precisely regulate the volume introduced through an inlet from based upon the number of strokes of the pump.

Any sample or solution that is chemically compatible with the elastomeric material from which the microfluidic device is fabricated can be introduced into the device. Once the elastomeric material has been molded or etched into the appropriate shape, it may be necessary to pre-treat the flow channel portion of the material in order to facilitate operation in connection with a particular application. For example, in order to reduce or prevent elastomer from dissolving in the solvent or reacting with a reagent or assaying solution, one can coat the inner walls of the flow channels with polypropylene, polyvinylidene fluoride, Viton® or other suitable inert materials.

D. Valves

1. Structure

The valves of the microfluidic devices provided herein are formed of elastomeric material and include an elastomeric segment (or membrane or separating portion) that separates a control channel and a flow channel. The valves have two general designs: those that are typically open and those that are normally closed. Valves that are typically open are actuated to block flow through a flow channel by applying pressure to the control channel, thereby deflecting the membrane into the flow channel to restrict flow. In the case of valves that are normally closed, the membrane or separating portion normally extends into the flow channel. However, upon reduction of pressure in the control channel relative to the flow channel, the membrane/separating portion is pulled into the control channel, thus removing the blockage in the flow channel.

Figure 1B:
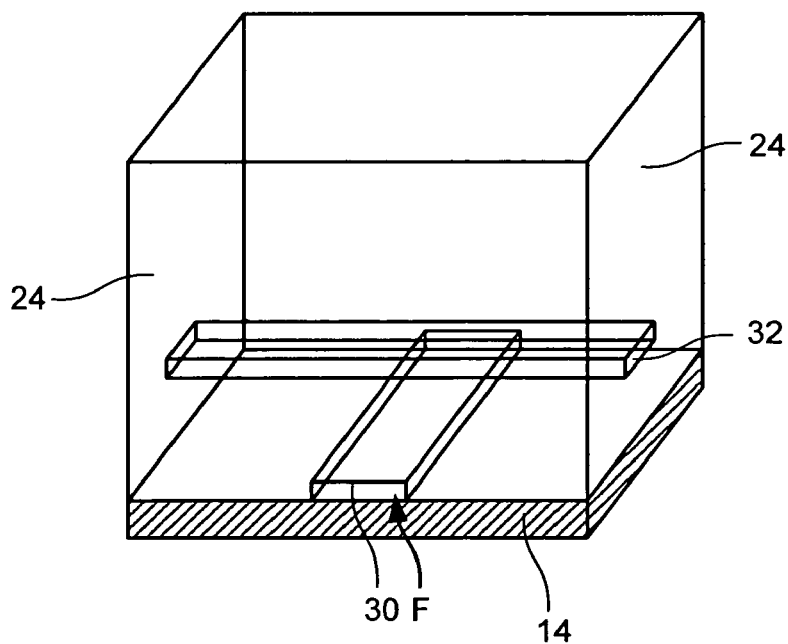
Figure 2A:
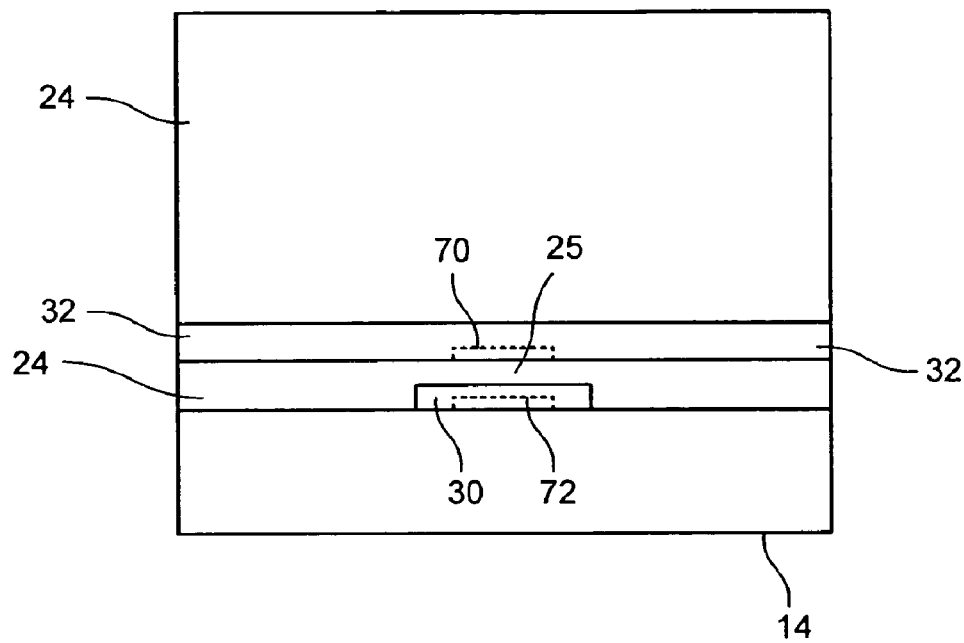
FIG. 2A is a sectional view of an elastomeric block showing the disposition of a flow and control channels with respect to one another in a valve and optional electrodes for actuating the valve.
Figure 2B:
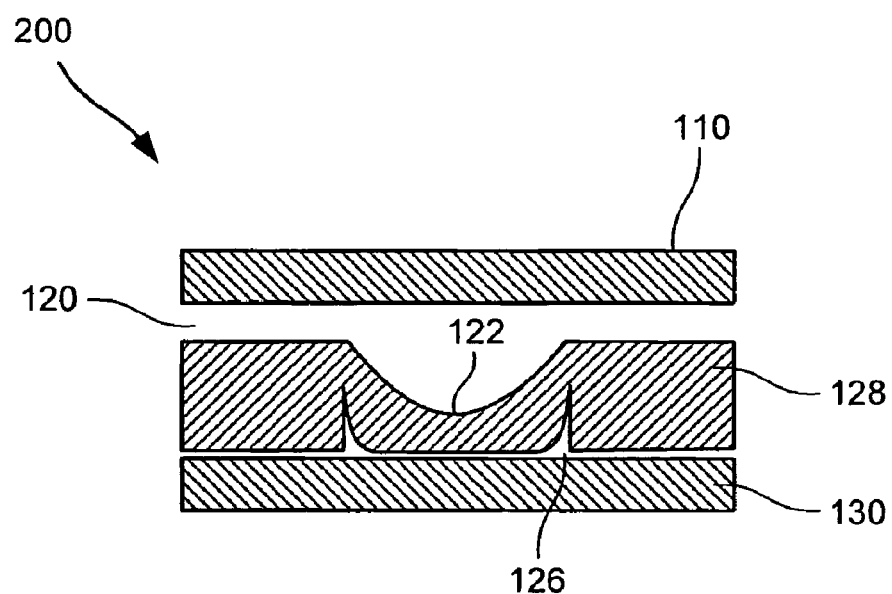
FIG. 2B is a sectional view of an elastomeric block showing blockage of a flow channel when a normally open valve is actuated.

FIGS. 1A and 1B illustrate the general elements of a valve that is typically open. As can be seen, elastomeric structure 24 contains a control channel 32 overlying recess 21 formed from a raised portion of a mold. When the recess in this elastomeric structure is sealed at its bottom surface to solid substrate 14, recess 21 forms a flow channel 30. As can be seen in FIG. 1B and FIG. 2A, flow channel 30 and control channel 32 are preferably disposed at an angle to one another with a small membrane 25 of elastomeric block 24 separating the top of flow channel 30 from the bottom of control channel 32. While these figures show control channels that extend across the device, it should be understood that this need not be the case. The control channel can be a recess sufficiently large such that the membrane is able to provide the desired level of blockage in the flow channel. FIG. 2B illustrates the situation for a normally open elastomeric valve structure 200 in which the valve has been actuated and the flow channel is blocked. In particular, the structure includes a control channel 120 formed within one elastomeric layer 110 that overlays another elastomeric layer 128 which includes a flow channel 126. Elastomeric layer 110 is attached to substrate 130. Because the control channel has been pressurized, the membrane 122 separating the control channel 120 and the flow channel 126 is deflected down into the flow channel 126, thereby effectively blocking solution flow therethrough. Once pressure is released, membrane 122 deflects back up from the flow channel 126 to allow solution flow.

Figure 3A:
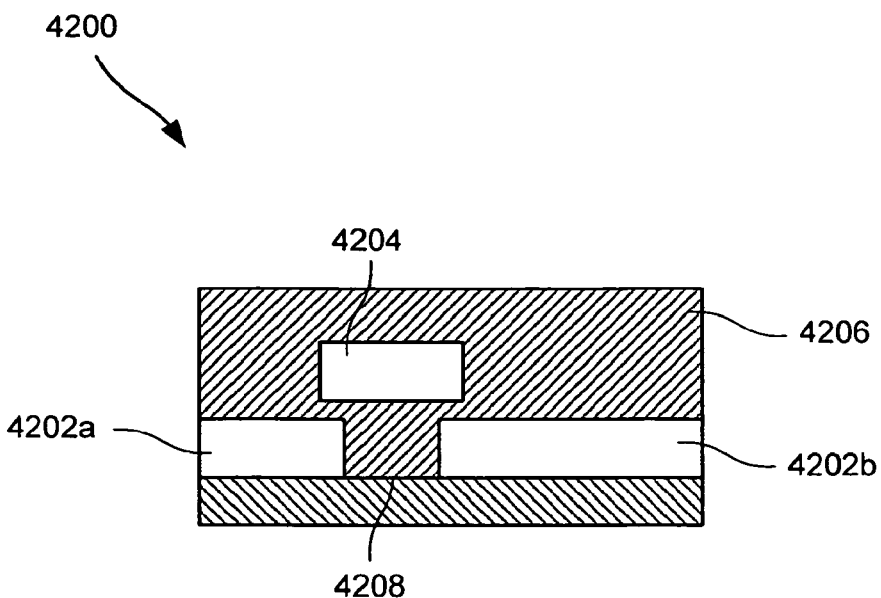
FIGS. 3A and 3B show one example of a normally-closed valve structure.
Figure 3B:
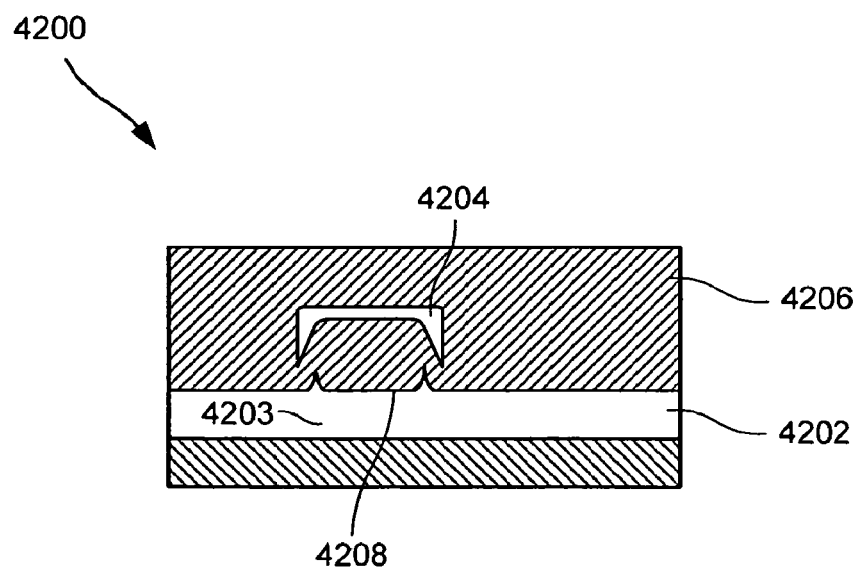

As noted above, the valves can also have a normally closed configuration. FIG. 3A illustrates one example of a normally-closed valve 4200 in an unactuated state. Flow channel 4202 and control channel 4204 are formed in elastomeric block 4206. Flow channel 4202 includes a first portion 4202a and a second portion 4202b separated by separating portion 4208. Control channel 4204 overlies separating portion 4208. As shown in FIG. 3A, in its relaxed, unactuated position, separating portion 4208 remains positioned between flow channel portions 4202a and 4202b, interrupting flow channel 4202. FIG. 3B shows a cross-sectional view of valve 4200 wherein separating portion 4208 is in an actuated position. When the pressure within control channel 4204 is reduced to below the pressure in the flow channel (for example by vacuum pump), separating portion 4208 experiences an actuating force drawing it into control channel 4204. As a result of this actuation force, membrane 4208 projects into control channel 4204, thereby removing the obstacle to solution flow through flow channel 4202 and creating a passageway 4203. Upon elevation of pressure within control channel 4204, separating portion 4208 assumes its natural position, relaxing back into and obstructing flow channel 4202.

It is not necessary that the elastomeric layers that contain the flow and control channels be made of the same type of elastomeric material. For example, the membrane that separates the control and flow channels can be manufactured from an elastomeric material that differs from that in the remainder of the structure. A design of this type can be useful because the thickness and elastic properties of the membrane play a key role in operation of the valve.

2. Options for Actuating Valves

A variety of approaches can be utilized to open or close a valve. If a valve is actuated by increasing pressure in a control channel, in general this can be accomplished by pressurizing the control channel with either a gas (e.g., air) or a fluid (e.g., water or hydraulic oils). However, optional electrostatic and magnetic actuation systems can also be utilized. Electrostatic actuation can be accomplished by forming oppositely charged electrodes (which tend to attract one another when a voltage differential is applied to them) directly into the monolithic elastomeric structure. For example, referring once again to FIG. 2, an optional first electrode 70 (shown in phantom) can be positioned on (or in) membrane 25 and an optional second electrode 72 (also shown in phantom) can be positioned on (or in) planar substrate 14. When electrodes 70 and 72 are charged with opposite polarities, an attractive force between the two electrodes will cause membrane 25 to deflect downwardly, thereby closing the "valve" (i.e., closing flow channel 30).

Alternatively, magnetic actuation of the flow channels can be achieved by fabricating the membrane separating the flow channels with a magnetically polarizable material such as iron, or a permanently magnetized material such as polarized NdFeB. Where the membrane is fabricated with a magnetically polarizable material, the membrane can be actuated by attraction in response to an applied magnetic field.

Optional electrolytic and electrokinetic actuation systems can also be utilized. For example, actuation pressure on the membrane can be generated from an electrolytic reaction in a recess overlying the membrane. In such an embodiment, electrodes present in the recess are used to apply a voltage across an electrolyte in the recess. This potential difference causes an electrochemical reaction at the electrodes and results in the generation of gas species, thereby giving rise to a pressure differential in the recess. Alternatively, actuation pressure on the membrane can arise from an electrokinetic fluid flow in the control channel. In such an embodiment, electrodes present at opposite ends of the control channel are used to apply a potential difference across an electrolyte present in the control channel. Migration of charged species in the electrolyte to the respective electrodes can give rise to a pressure differential.

Finally, valves can be actuated the device by causing a fluid flow in the control channel based upon the application of thermal energy, either by thermal expansion or by production of gas from liquid. Similarly, chemical reactions generating gaseous products may produce an increase in pressure sufficient for membrane actuation.

3. Options for Selectively Actuating Valves

In order to facilitate fabrication and to reduce the number of control channels in a microfluidic device, often a control channel overlays a number of flow channels. In such instances, pressurization of such a control channel could cause blockage of all the flow channels. Often it is desired to block only selected flow channels, rather than all the flow channels which a control channel abuts. Selective actuation can be achieved in a number of different ways.

One option illustrated in FIG. 4 is to control the width of the control channels 5004, 5006 at the point at which they extend across the flow channels 5002A and 5002B. In locations where the control channels are wide 5004A, 5006A, pressurization of the control channel 5004, 5006 causes the membrane separating the flow channel and the control channel to depress significantly into the flow channel 5002A, 5002B, thereby blocking the flow passage therethrough. Conversely, in the locations where the control line is narrow 5004B, 5006B, the membrane separating the channels is also narrow. Accordingly, the same degree of pressurization will not result in membrane becoming depressed into the flow channel 5002A, 5002B. Therefore, fluid passage thereunder will not be blocked.

The same general effect can be obtained by varying the width of the flow channel relative to the control channel. Incorporation of an elastomeric support in the section of the flow channel opposite the membrane that is deflected into the flow channel can also prevent complete stoppage of solution flow.

Valves in certain of the figures are represented by single dashed lines if the valve can be utilized to block solution flow through the flow channel. A control channel that crosses a flow channel but which does not act to block the flow channel (for the reasons just described) is represented by a solid arch that arches over a flow channel.

Various other methods of actuating valves are described in the above incorporated U.S. and PCT applications.

E. Pumps

Figure 5A:
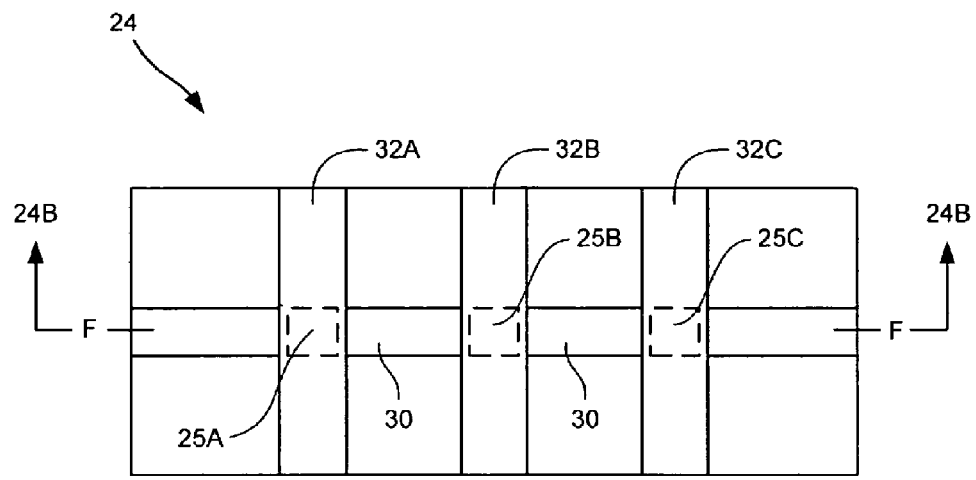
FIGS. 5A and 5B illustrate one example of a peristaltic pump.
Figure 5B:
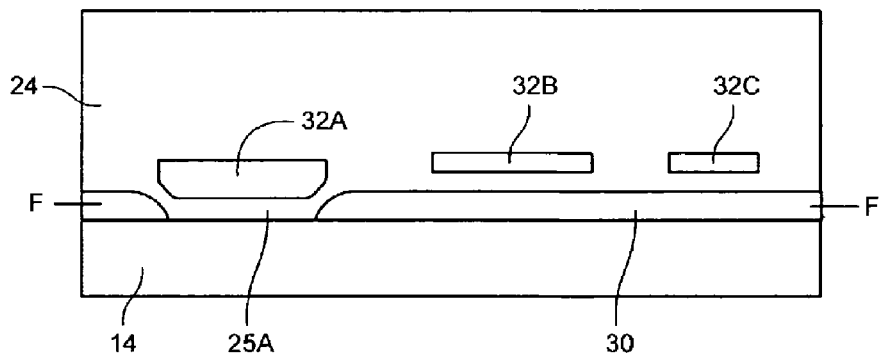

The pumps integrated within the microfluidic devices described herein can be formed from a plurality of control channels that overlay a flow channel. A specific example of a system for peristaltic pumping is shown in FIGS. 5A and 5B. As can be seen, a flow channel 30 has a plurality of generally parallel control channels 32A, 32B and 32C passing thereover. By pressurizing control line 32A, flow F through flow channel 30 is shut off under membrane 25A at the intersection of control line 32A and flow channel 30. Similarly, (but not shown), by pressurizing control line 32B, flow F through flow channel 30 is shut off under membrane 25B at the intersection of control line 32B and flow channel 30, etc. Each of control lines 32A, 32B, and 32C is separately addressable. Therefore, peristalsis can be actuated by the pattern of actuating 32A and 32C together, followed by 32A, followed by 32A and 32B together, followed by 32B, followed by 32B and C together, etc. Pumps of this type are denoted in shorthand form in certain of the figures with a series of three parallel dashed lines.

External pumps can also be connected to a flow channel to transport solutions through a channel. Alternatively, a vacuum can be applied to a flow channel to direct fluid flow toward the region of reduced pressure.

IV. High Throughput Screening Systems

A. General

In their simplest forms, the biochemical system models employed in the methods and microfluidic devices of the present invention will screen for an effect of a test compound on an interaction between two components of a biochemical system, i.e., ligand-antiligand interaction, for example, antibody-antigen interaction, enzyme-substrate interaction, and the like. In this form, the biochemical system model will typically include the two normally interacting components of the system for which an effector is sought, e.g., the antibody and its protein substrate or the enzyme and its substrate.

Determining whether a sample has an effect on this interaction then involves contacting the ligand with the sample and assaying for the ligand-antiligand interaction. The assayed function can be then compared to a control, e.g., the same reaction in the absence of the antiligand or in the presence of a known antiligand.

Although described in terms of two-component biochemical systems, the methods and microfluidic devices of the present invention can also be used for more complex systems where the result of the system is known and assayable at some level, e.g., enzymatic pathways, cell signaling pathways and the like. Alternatively, the methods and microfluidic devices described herein can be used to screen for compounds that interact with a single component of a biochemical system, e.g., compounds that specifically bind to a particular biochemical compound, e.g., a receptor, enzyme, nucleic acid, etc.

Ligand can also be embodied in whole cell systems. For example, where one is seeking to screen test compounds for an effect on a cellular response, whole cell may be utilized by immobilizing the cell on the solid substrate surface. Modified cell systems can also be employed in the microfluidic devices encompassed herein. For example, chimeric reporter systems can be employed as indicators of an effect of a sample on a particular biochemical system. Chimeric reporter systems typically incorporate a heterogenous reporter system integrated into a signaling pathway which signals the binding of a receptor to its substrate. For example, a receptor can be fused to a heterologous protein, e.g., an enzyme whose activity is readily assayable. Activation of the receptor by substrate binding then activates the heterologous protein which then allows for detection. Thus, the surrogate reporter system produces an event or signal which is readily detectable, thereby providing an assay for receptor/substrate binding. Examples of such chimeric reporter systems have been previously described in the art.

Additionally, where one is screening for bioavailability, e.g., transport, biological barriers can be included. The term "biological barriers" generally refers to cellular or membranous layers within biological systems, or synthetic models thereof. Examples of such biological barriers include the epithelial and endothelial layers, e.g. vascular endothelia and the like.

Biological responses are often triggered and/or controlled by the binding of a receptor to its substrate. For example, interaction of growth factors, i.e., EGF, FGF, PDGF, etc., with their receptors stimulates a wide variety of biological responses including, e.g., cell proliferation and differentiation, activation of mediating enzymes, stimulation of messenger turnover, alterations in ion fluxes, activation of enzymes, changes in cell shape and the alteration in genetic expression levels. Accordingly, control of the interaction of the receptor and its substrate can offer control of the biological responses caused by that interaction.

Accordingly, in one aspect, the present invention is useful in screening for compounds that affect an interaction between a receptor and its substrates. Thus, a receptor/substrate pair can include a typical protein receptor, usually membrane associated, and its natural substrate, e.g., another protein or small molecule. Receptor/substrate pairs can also include antibody/antigen binding pairs, complementary nucleic acids, nucleic acid associating proteins and their nucleic acid ligands. A large number of specifically associating biochemical compounds are well known in the art and can be utilized in practicing the present invention. In addition, ternary or higher binding complexes can also be assayed using microfluidic devices of the present invention as discussed in detail below.

Traditionally, methods for screening for effectors of a receptor/substrate interaction have involved incubating a receptor/substrate binding pair in the presence of a sample. The level of binding of the receptor/substrate pair is then compared to negative and/or positive controls. Where a decrease in normal binding is seen, the sample is determined to be an antagonist or inhibitor of the receptor/ligand binding. Where an increase in that binding is seen, the substrate is determined to be an agonist of the interaction.

A similar, and perhaps overlapping, set of biochemical systems includes the interactions between enzymes and their substrates. Typically, effectors of an enzyme's activity toward its substrate are screened by contacting the enzyme with a substrate in the presence and absence of the compound to be screened and under conditions optimal for detecting changes in the enzyme's activity. After a set time for reaction, the mixture is assayed for the presence of reaction products or a decrease in the amount of substrate. The amount of substrate that has been catalyzed is then compared to a control, i.e., enzyme contacted with substrate in the absence of sample or presence of a known effector. As above, a compound that reduces the enzymes activity toward its substrate is termed an "inhibitor" or "antagonist" whereas a compound that accentuates that activity is termed an "agonist."

Generally, the various screening methods encompassed by the present invention involve a simultaneous introduction of a plurality of samples into a microfluidic device. Typically, each sample is introduced to each of one of the plurality of first or the second flow channels. Once injected into the device, each sample is assayed simultaneously to provide a high throughput screening.

As used herein, the term "sample" refers to the collection of compound(s) that are to be screened for their ability to bind to immobilized ligand or affect a particular immobilized biochemical system. Samples can include a wide variety of different compounds, including chemical compounds, mixtures of chemical compounds, e.g., polysaccharides, small organic or inorganic molecules, biological macromolecules, e.g., peptides, proteins, nucleic acids, or an extract made from biological materials such as bacteria, plants, fungi, or animal cells or tissues, naturally occurring or synthetic compositions. Depending upon the particular embodiment being practiced, the samples can be provided, e.g., injected, free in solution, or can be attached to a carrier, or a particle, e.g., beads. A number of suitable particles can be employed to attach the samples. Examples of suitable particles include agarose, cellulose, dextran (commercially available as, i.e., Sephadex, Sepharose) carboxymethyl cellulose, polystyrene, polyethylene glycol (PEG), filter paper, nitrocellulose, ion exchange resins, plastic films, glass beads, polyaminemethylvinylether maleic acid copolymer, amino acid copolymer, ethylene-maleic acid copolymer, nylon, silk, etc. Additionally, for the methods and microfluidic devices described herein, samples can be screened individually, or in groups. Group screening is particularly useful where hit rates for effective samples are expected to be low such that one would not expect a large positive result for a given group.

One exemplary area where high throughput is important is in proteomics. Cells express thousands of proteins at different concentrations. The behavior and interaction of these proteins is dependent upon the cell type, the stage of the cell cycle, and extracellular events, to name a few. Proteins are also chemically modified by cellular machinery, and this modification further differentiates their behavior and interaction with other proteins. Important factors in protein studies include concentration and post-translational modification. The differences in these factors between cell populations can be detected by antibody detection. In one embodiment of the present invention, an antibody (i.e., ligand) that recognizes a particular protein of interest or the antigen (i.e, antiligand) is immobilized on a surface. A cellular protein sample is then washed over the immobilized antibody, which recognizes and binds the antigen at high affinity. A second antibody or detection antibody (i.e., a labeled ligand) that also recognizes the antigen is added to the solution and also binds the selected antigen. In this manner, a sandwich assay can be performed where a chemiluminescent or fluorescent detector recognizes the detection antibody. The bound detectors are separated from the unbound detectors by washing. The concentration of the detectors is proportional to the concentration of bound antigen.

B. Use of Microfluidic Devices in Highthroughput Assay

As indicated supra, the foregoing elements or modules of microfluidic devices can be combined in a large number of configurations and utilized in a wide variety of applications. Exemplary designs useful for conducting certain types of assays are described in this section. It should be understood, however, that the microfluidic devices of the present invention are not limited to these particular configurations.

Microfluidic devices of the present invention include a plurality of first flow channels and a plurality of second flow channels. Each of the first flow channels intersect with, and are in fluid communication with, each of the second flow channels. The devices are typically used such that ligand(s) are attached to the solid substrate surface by introducing into each of the first flow channels while blocking flow through the second flow channels. Alternatively, the ligand(s) can be pre-attached to the solid substrate surface prior to attaching the solid substrate to the elsatomeric layer.

Figure 6:
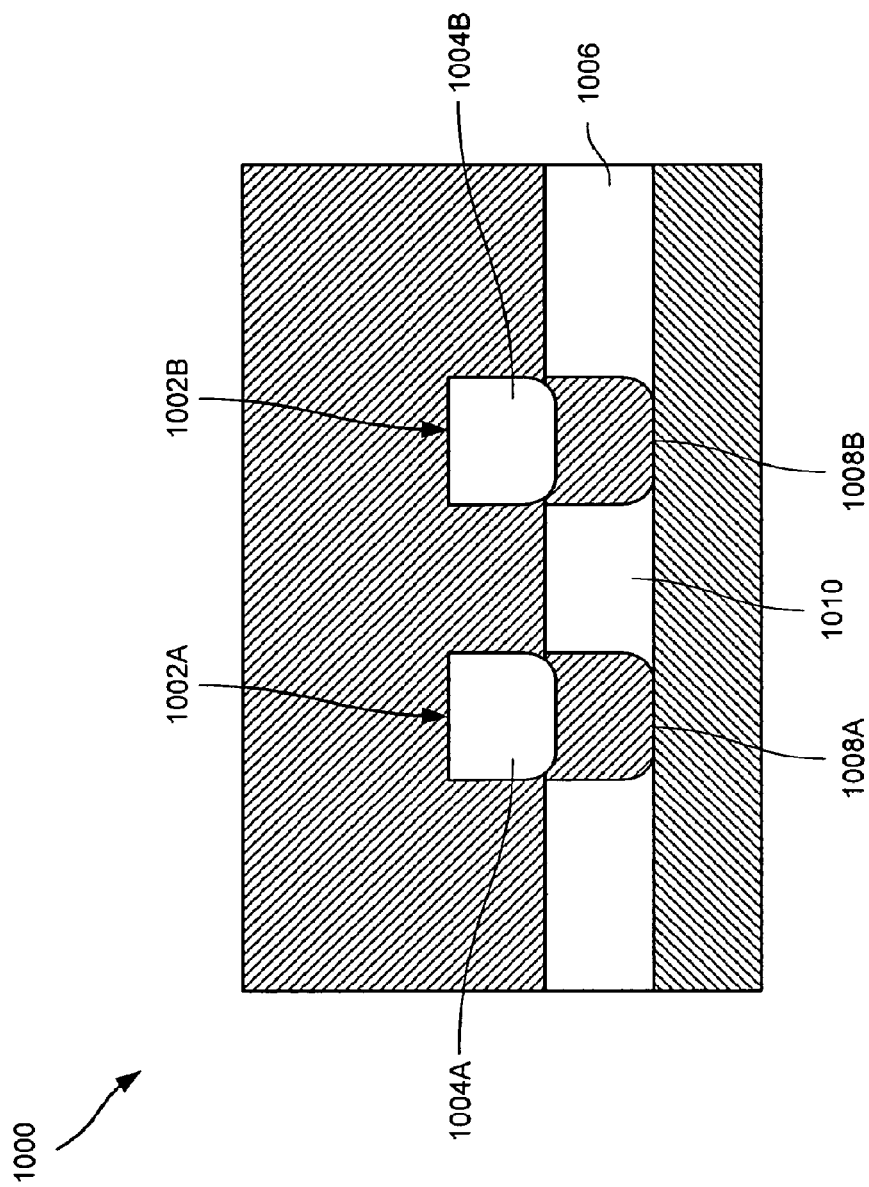
FIG. 6 is a cross-sectional view that illustrates the formation of a holding space within a flow channel upon actuation of valves in the flow channel.

Once the ligand(s) are attached to the solid substrate surface, flow through the first flow channels is blocked. Sample(s) are subsequently introduced into each of the second flow channels, typically such that different samples are introduced into different second flow channels. Optionally, loop forming valves are actuated such that each pair of the second flow channels forms a looped flow channel. The sample(s) are then circulated through each of the looped flow channels using a recirculating pump. Alternatively, first control valves and the second control valves are simultaneously actuated to form a plurality of holding spaces each encapsulating one intersecting area. FIG. 6 illustrates a holding space that is formed along one of the flow channels (flow channel intersecting area is not shown). These two methods allow a prolonged contact between the sample(s) and the solid substrate-bound ligand. The sample(s) in the intersecting areas are subsequently reacted with the solid substrate-bound ligand in the intersecting areas of the first and the second flow channels.

Regardless of the particular design, a large number of samples can be rapidly screened within a short time period because separate reactions can simultaneously be conducted in each of the flow channel intersecting areas.

Typically, the pumps are utilized for transporting fluids within the flow channels.

C. Exemplary Devices

Figure 7B:
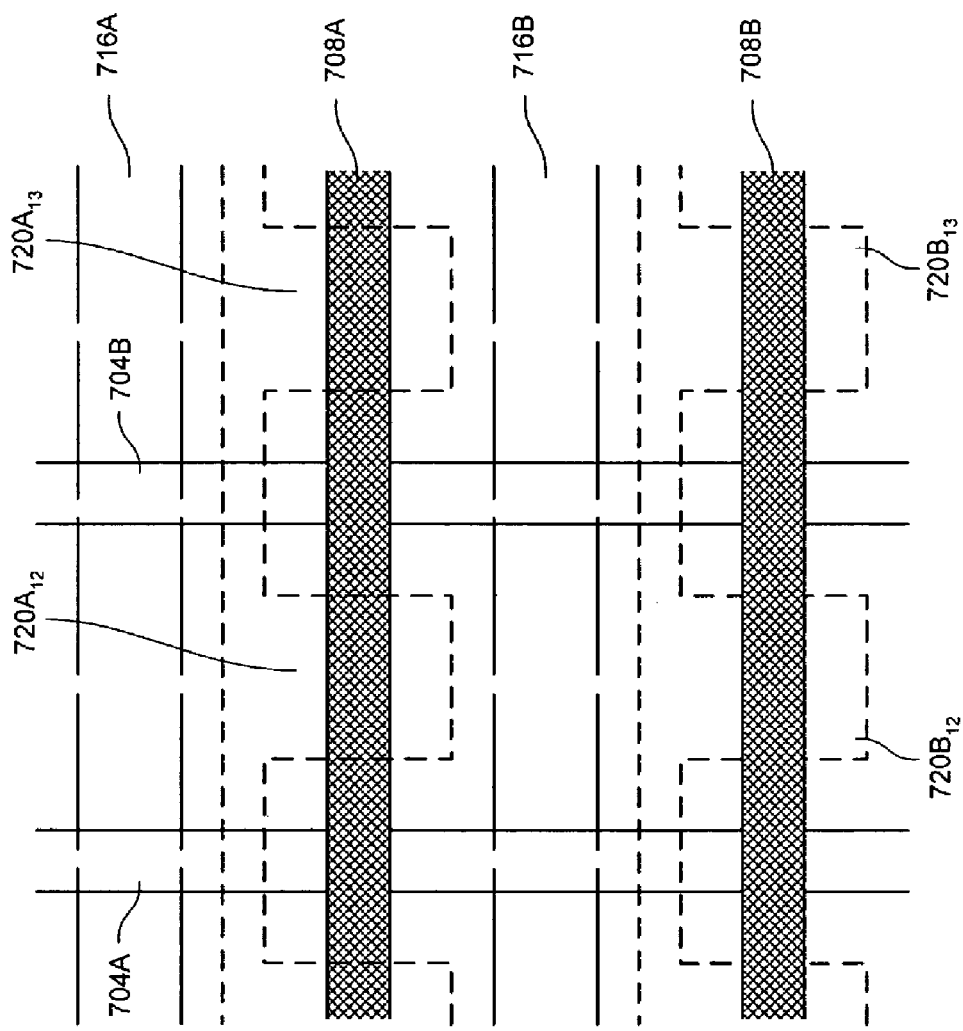
Figure 7C:
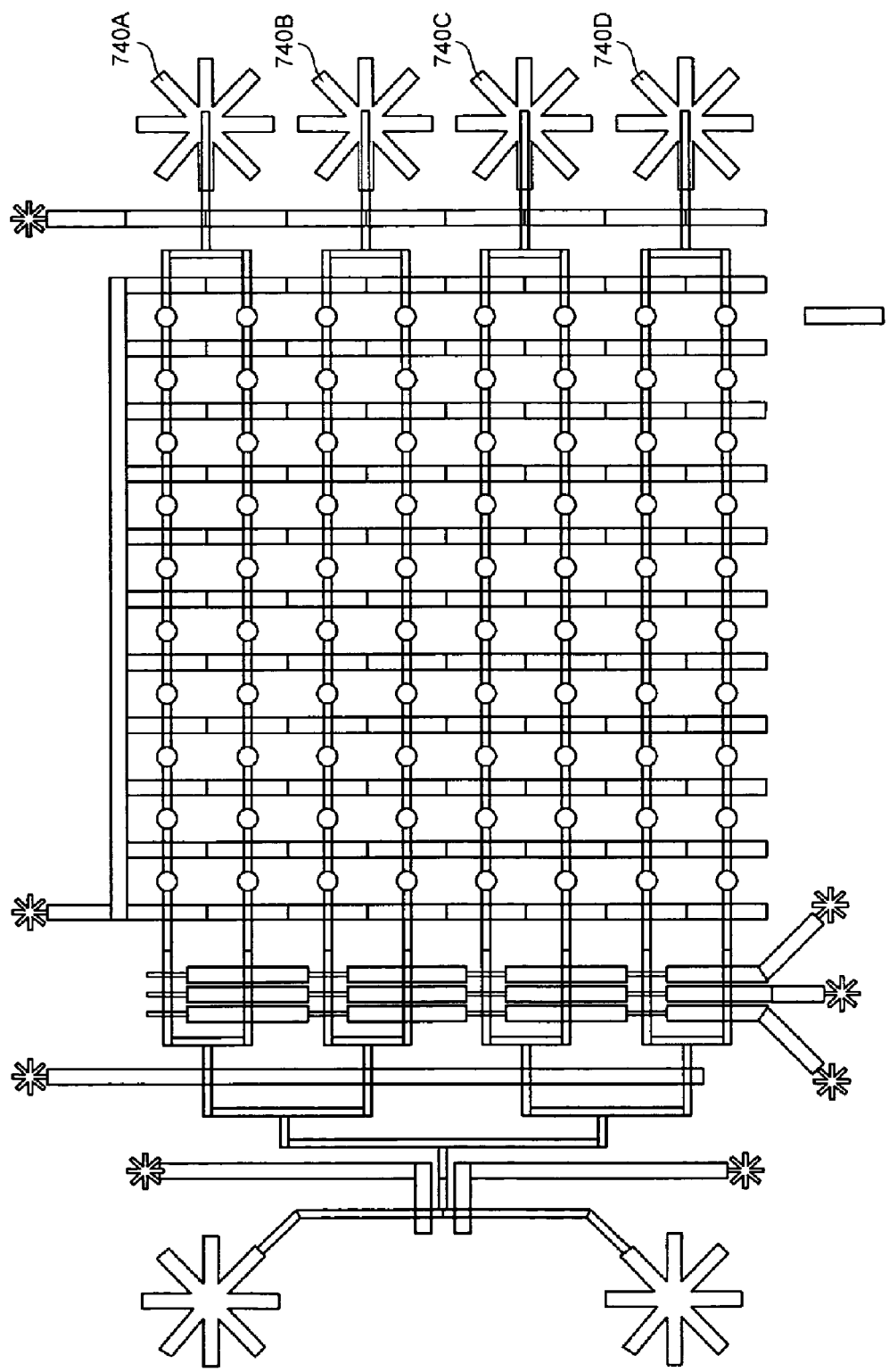
Figure 7E:
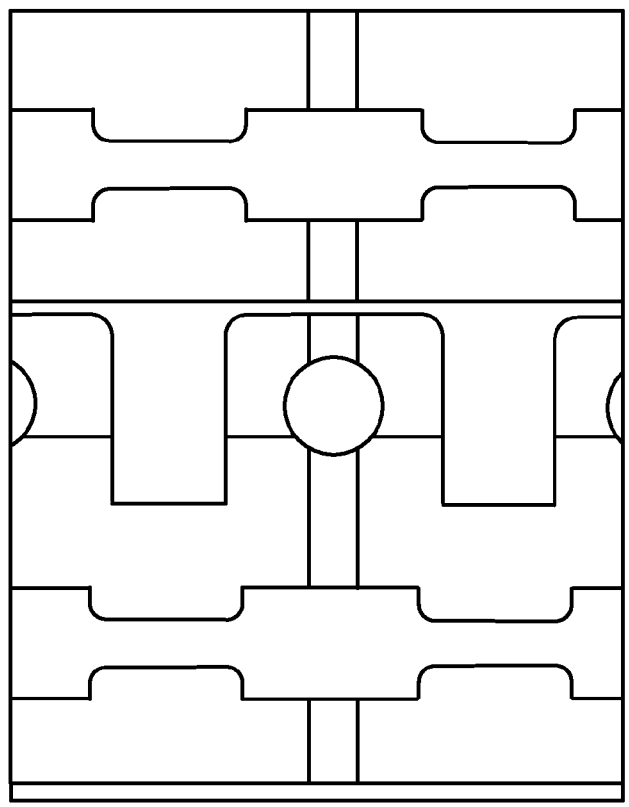
Figure 7D:
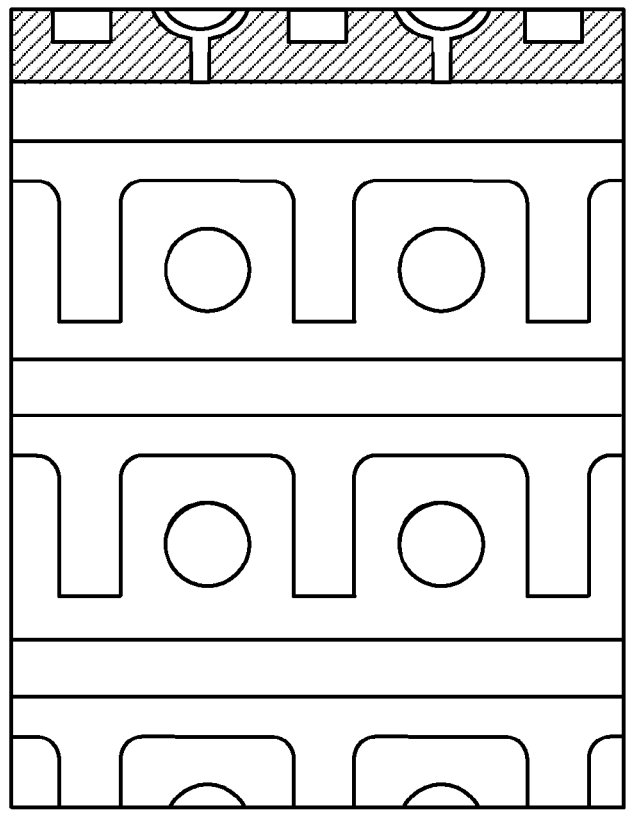

One specific example of a microfluidic device that can be used in high throughput assaying applications is illustrated in FIG. 7A. The device includes a plurality of first flow channels 704A-H (yellow) and a plurality of second flow channels 708A-C (pink). These flow channels intersect one another resulting in a plurality of channel intersections 712A-BD. It should be noted that the second flow channels 708A-C branches off and rejoins near the outlet, thus forming a pair of branched flow channels $708A_{1-2}$, $708B_{1-2}$, and $708C_{1-2}$. These pair of branched flow channels form looped flow channels when control valves 724A and 724B are closed. The channel intersections 712A-BD can optionally comprise a chamber (also called reservoir or well) which is present when a via layer is used. See Example 1 below. The device includes a plurality of first control valves 716A-G and a plurality of second control valves $720A_{11}$-$G_{19}$ to regulate flow of solution through the first flow channels and the second flow channels, respectively. In this way, the flow of solution can be controlled to prevent the solution from one flow channel contaminating or mixing with the solution in another flow channel. Also shown is are loop forming control valves 724A-B and a recirculating pump 728. In FIG. 7A, one of the loop forming control valve 724B also functions as a pump 732, which is discussed in detail below. The loop forming control valves 724A and 724B allow circulation of a solution through the looped flow channel by the action of recirculating pump 728. The device also includes optional pumps 732 and 736, which are used to transport solutions through the second and the first flow channels, respectively. Shown in FIG. 7C are optional chambers 740A-D for solutions that are introduced into the second flow channels.

Referring again to FIG. 7A, in operation, to introduce ligand(s), valves 716A-G are opened and valves $720A_{11}$-$720G_{19}$ are closed, and appropriate reagent solution(s) are introduced into the first flow channels 704A-H via corresponding inlets to attach ligand(s) onto the solid substrate surface. As indicated above, alternatively, ligand(s) can be attached to the solid substrate surface prior to attaching the elastomeric layer to the solid substrate, in which case samples are introduced into the first flow channels. Pump 736 can be utilized to control the rate of solution flow through the first flow channels 704A-H. After attaching the ligands onto the solid substrate surface (or after forming ligand/antiligand complex(s)), the first flow channels are optionally washed to remove unattached ligand(s) (or unbound samples).

Sample(s) to be screened (or labeled ligand(s)) are introduced by closing first control valves 716A-G to restrict solution flow through the first flow channels 704A-H while opening the second control valves $720A_{11}$-$G_{19}$. Sample(s) (or labeled ligand(s)) are introduced into the second flow channels 708A-C. The sample(s) (or labeled ligand(s)) can be continuously flowed through the second flow channels or the loop forming control channels 724A and 724B can be closed to form a plurality of looped flow channels from each pair of second flow channels 708. The sample can then be circulated through the looped flow channels using the recirculating pumps 728.

Alternatively, the first control valves 716A-G can also be closed thereby forming a plurality of channel intersections 712A-BD. In this manner, samples (or labeled ligand(s)) are held within the channel intersections 712A-BD to provide a prolonged contact with the solid substrate-bound ligand (or the ligand/antiligand complex). FIG. 7B shows position of the first and the second control valves relative to the flow channel intersecting areas. By actuating both of the first and the second control valves, a holding space is formed within each flow channel intersecting areas.

Thereafter, the second flow channels 708A-C are optionally rinsed to remove the unbound sample(s) (or labeled ligand(s)). If the first flow channels are used to attach ligand(s) to the solid substrate surface, a labeled ligand can optionally be introduced to either the first or the second flow channels to perform a sandwich assay, such as ELISA, FLISA, etc.

After assaying is completed, the elastomeric layer is removed from the solid substrate surface. And the solid substrate is then analyzed with an appropriate analyzer to determine the result.

D. Samples (i.e., Test Compounds)

The assay and screening methods described herein can be conducted with essentially any compound. In general terms, the test agent or test compound is potentially capable of interacting with the component being assayed (e.g., cell, enzyme, receptor, antibody, cellular organelle). In cellular assays, for example, the component of the cell with which the test compound potentially interacts can be any molecule, macromolecule, organelle or combination of the foregoing that is located on the surface of the cell or located within the cell. For example, if one is screening for compounds capable of interacting with certain cellular receptors, the test agents are selected as potentially able to interact with the receptors of interest (e.g., binding at the binding site of the receptor or affecting binding at the binding site of the receptor, such as an agonist or antagonist). In certain two-hybrid assays (see infra), the test agent is one that is potentially able to influence the binding interaction between the binding proteins of the two fusions (see below).

Consequently, test agents can be of a variety of general types including, but not limited to, polypeptides; carbohydrates such as oligosaccharides and polysaccharides; polynucleotides; lipids or phospholipids; fatty acids; steroids; or amino acid analogs. Further, the compounds can be growth factors, hormones, neurotransmitters and vasodilators, for example. Likewise, the compounds can be of a variety of chemical types including, but not limited to, heterocyclic compounds, carbocyclic compounds, β-lactams, polycarbamates, oligomeric-N-substituted glycines, benzodiazepines, thiazolidinones and imidizolidinones. Certain test agents are small molecules, including synthesized organic compounds.

Test agents can be obtained from libraries, such as natural product libraries or combinatorial libraries, for example. A number of different types of combinatorial libraries and methods for preparing such libraries have been described, including for example, PCT publications WO 93/06121, WO 95/12608, WO 95/35503, WO 94/08051 and WO 95/30642, each of which is incorporated herein by reference.

V. Combinatorial Synthesis

A. Methods

Microfluidic devices having the general arrangement of components as described for high throughput assays, particularly as depicted in FIGS. 6A and 6B, can also be utilized to conduct combinatorial chemical synthesis. The methods generally parallel those described supra for the high throughput screening, except that instead of ligands and samples being introduced into the flow channels different reactants are introduced instead.

Thus, instead of attaching ligand(s), monomer(s) or appropriate linker(s) are attached to the solid substrate and suitably protected monomer(s) are introduced. By selective performing deprotection, coupling reactions sequentially, one can achieve a wide variety of combinatorial chemical synthesis.

Further guidance regarding combinatorial methods is provide in PCT publications WO 93/06121, WO 95/12608, WO 95/35503, WO 94/08051 and WO 95/30642, each of which is incorporated herein by reference.

B. Compounds

The compounds generated by such methods can be composed of any components that can be joined to one another through chemical bonds in a series of steps. Thus, the components can be any class of monomer useful in combinatorial synthesis. Hence, the components, monomers, or building blocks (the foregoing terms being used interchangeably herein) can include, but are not limited to, enzymes or enzyme modules, amino acids, carbohydrates, lipids, phospholipids, carbamates, sulfones, sulfoxides, esters, nucleosides, heterocyclic molecules, amines, carboxylic acids, aldehydes, ketones, isocyanates, isothiocyanates, thiols, alkyl halides, phenolic molecules, boronic acids, stannanes, alkyl or aryl lithium molecules, Grignard reagents, alkenes, alkynes, dienes and urea derivatives. The type of components added in the various steps need not be the same at each step, although in some instances the type of components are the same in two or more of the steps. For example, a synthesis can involve the addition of different amino acids at each cycle; whereas, other reactions can include the addition of amino acids during only one cycle and the addition of different types of components in other cycles (e.g., aldehydes or isocyanates).

Given the diversity of components that can be utilized in the methods of the invention, the compounds capable of being formed are equally diverse. Essentially molecules of any type that can be formed in multiple cycles in which the ultimate compound or product is formed in a component-by-component fashion can be synthesized according to the methods of the invention. Examples of compounds that can be synthesized include polypeptides, polyketides, oligosaccharides, polynucleotide, phospholipids, lipids, benzodiazepines, thiazolidinones and imidizolidinones. As noted above, the final compounds can be linear, branched, cyclic or assume other conformations. The compounds can be designed to have potential biological activity or non-biological activity.

VI. Variations

A. Channel Coatings

In certain methods, the flow channels are coated or treated with various agents to enhance certain aspects of the assay. For example, depending upon the nature of the material from which the flow channels are formed, it can be useful to coat the flow channels with an agent that protects against or prevents components of the assay (for example cells, proteins, peptides, substrates, small molecules) from adhering to the walls of the flow channels or to the sides of the wells through which these agents are introduced into the device. One function of these coatings is to help ensure the biological integrity of the introduced sample. Another function is to prevent physical interactions between cells and the walls of the channel that might affect cellular responses or functions in undesired ways. Examples of suitable coating agents include, but are not limited to, TEFLON, parylene, acrylamides, polyethylene glycol, silanes, and other agents to form self-assembled monolayers.

Similarly, channels can be modified with a variety of agents to achieve other purposes such as separation and sorting functions, with the goal being to prepare the flow channels in accordance with the particular application being conducted. More specifically, by properly selecting the bulk matrix of the flow channel (i.e., the particular choice of elastomers to utilize in constructing the flow channels), surface chemistry (i.e., modification of the properties of microchannels created within the elastomer) and the specific modification of regions of the elastomer surface (e.g., by covalent and/or non-covalent attachment of proteins, peptides, nucleic acids (or their analogs), lipids, carbohydrates) can facilitate the "tuning" of the device to a given application or combination of applications. Methods for modification of elastomer surfaces include, but are not limited to: (1) copolymerization with functional groups during elastomer curing (an example of bulk modification), (2) oxygen plasma treatment (3) modification of plasma-treated surfaces with silanizing reagents (e.g., 3-aminopropyltriethoxysilane, N-(2-aminoethyl)-3-aminopropyltrimethoxysilane, dimethylchlorosilane or hexamethyldisilazane) which form self-assembled monolayers on the elastomer surface (which can be used to treat individual flow channels), (4) use of photochemical crosslinking reagents to create patterns of reactive groups on the elastomer surface (e.g., aryl azide derivatives or quinone-based derivatives), (5) passive modification of the elastomer surface by adsorption.

Adsorption also enables one to create secondary or tertiary layers of modification that offer improved properties over primary adsorption. As a specific example, one can use antibodies against an antigen to create a primary coating of flow channel walls. If antigen is then bound to the bound antibody, one can then create a secondary layer of specifically bound antigen. Antigen bound in this way can be "presented" to the interior of the flow channel in a more appropriate way than as a passively adsorbed primary layer. Schemes for creating a plurality of layers composed of proteins, nucleic acids, lipids or carbohydrates or combinations thereof will be apparent to the skilled practitioner.

Channels can also be coated with materials that specifically bind to assay components and/or reaction products such as products produced by a cell or during an enzymatic assay, for instance. One example of such a coating is one in which the channel is coated with a metal or a metal-derivatized material. Reaction products bearing a metal chelate tag thus become bound to the metal-coated wall or material. Of course, a wide variety of other binding pairs could also be utilized as substitutes for the metal chelating agent and metal. Assays utilizing such metal-derivatized materials is discussed in greater detail infra on the section on enzymatic assays (see also U.S. Pat. No. 6,146,842).

B. Doping Channels with Magnetic Materials

The flow channel elastomeric walls can optionally be doped with magnetic materials or by integration of a preformed magnet or electromagnet into the microfluidic device. Examples of magnetic materials that can be incorporated include magnetically polarizable materials such as iron and permanently magnetized materials. Inclusion of such materials within the flow channel enables magnetic based separations to be performed. External magnets that rotate can in some instances be used to facilitate mixing.

C. Electrodes

The flow channels can also optionally include electrodes to provide an additional type of control over agent and solution transport. Integration of electrodes into the devices permits electrophoretic separations or electroosmotic flow to be integrated with pump-driven transport. Suitable electrodes can be formed by sputtering a thin layer of metal (e.g., gold) onto a surface in a flow channel. Other metallization approaches such as chemical epitaxy, evaporation, electroplating, and electroless plating can also be utilized to form the necessary conductive material. Physical transfer of a metal layer to the surface of the elastomer is also available, for example by evaporating a metal onto a flat substrate to which it adheres poorly, and then placing the elastomer onto the metal and peeling the metal off of the substrate. A conductive electrode can also be prepared by depositing carbon black (e.g., Cabot Vulcan XC72R) on the elastomer surface, either by wiping on the dry powder or by exposing the elastomer to a suspension of carbon black in a solvent which causes swelling of the elastomer, (such as a chlorinated solvent in the case of PDMS).

VII. Exemplary Applications

The microfluidic devices disclosed herein can be utilized to conduct a variety of different assays. Essentially any biological assay or library screening application can be performed with the microfluidic devices that are described herein, provided none of the components of the assay or screen are incompatible with the size of the microfluidic channels. For example, microfluidic devices of the present invention can be used in proteomics to identify the presence of a particular protein or to screen for any agents that affect the activity of any class of "druggable" targets (i.e., a target that is able to be modulated by a small molecule to produce a desired phenotypic change in cell targets). Potential druggable targets include, but are not limited to, G-protein coupled receptors (GPCRs), cytokines and cytokine receptors, nuclear receptors (ligand-dependent transcription factors), signaling processes (e.g., receptor-ligand interactions, calcium mobilization, kinases and phosphatases, second messengers and transcription factors), proteases, ion channels, and determinants of cytotoxicity (e.g., pro- and anti-apoptotic processes and cell death). These targets can be addressed by the various types of assays, including, for example, fluorescent detection technologies such as fluorescence intensity determinations, fluorescence polarization, fluorescence resonance energy transfer, time-resolved techniques and fluorescence correlation spectroscopy.

The following include a non-exhaustive list of illustrative assays that can be conducted with the microfluidic devices provided herein, and illustrate the nature of the targets that can be investigated and the types of detection schemes that can be utilized.

A. Binding Assays

1. General

A wide variety of binding assays can be conducted utilizing the microfluidic devices disclosed herein. Interactions between essentially any ligand and antiligand can be detected. Examples of ligand/antiligand binding interactions that can be investigated include, but are not limited to, enzyme/ligand interactions (e.g., substrates, cofactors, inhibitors); receptor/ligand; antigen/antibody; protein/protein (homophilic/heterophilic interactions); protein/nucleic; DNA/DNA; and DNA/RNA. Thus, the assays can be used to identify agonists and antagonists to receptors of interest, to identify ligands able to bind receptors and trigger an intracellular signal cascade, and to identify complementary nucleic acids, for example. Assays can be conducted in direct binding formats in which a ligand and putative antiligand are contacted with one another or in competitive binding formats well known to those of ordinary skill in the art.

Because the microfluidic devices typically include a plurality of flow channels and intersecting areas that allow multiple analyses to be conducted at the same time, a large number of assays can be conducted in a short period. Active ligands or antiligands can be identified on the basis of the distinguishable labels. For example, assays can be conducted using labels that can be distinguished by physical, chemical, visual, radioactive, or other means. More specifically, labels can be distinguished from one another on the basis of different composition, size, color, shape, magnetic properties, chemical properties, electronic properties, fluorescent emission, for example. Specific examples of labels that can be distinguished on the basis of different fluorescent emissions are Luminex beads (Luminex Corporation) and Quantum dots (Quantum Dot Corporation). Sorting and/or quantitation is based upon label size, wavelength and/or amount of signal generated (e.g., fluorescence).

Binding assays generally involve contacting a solution containing ligands with a solution containing antiligands and allowing the solutions to remain in contact for a sufficient period such that binding partners form complexes. The ligand and/or antiligand is usually labeled. Alternatively, and in some preferred embodiments, a sandwich assay in which a labeled ligand is introduced to form ligand/antiligand/labeled ligand complex. Any of a variety of different labels can be utilized as described above. Ligands and antiligands are typically contacted within the intersecting areas of the flow channel. Solutions containing the ligands and antiligands can be incubated by circulating the solutions within the looped flow channels or holding the solution within the holding spaces as described supra. Complexes typically are detected by removing the solution and peeling the elastomeric layer away from the solid substrate and analyzing the intersecting areas of the solid substrate with an appropriate detector. Alternatively, complexes can be detected with the elastomeric layer still in contact with the solid substrate and analzying the intersecting areas of the solid substrate with an appropriate detector. The type of detector and detection method utilized depends upon the type of label used to label the ligand or antiligand.

2. Exemplary Binding Assay Process

Binding assays of the present invention typically involve a step in which complexes are separated from unreacted agents so that labeled complexes can be distinguished from uncomplexed labeled reactants. Often it is achieved by attaching either the ligand or antiligand to a support. After ligands and antiligands have been brought into contact, uncomplexed reactants are washed away and the remaining complexes subsequently detected.

The assays performed with the microfluidic devices disclosed herein generally involve contacting a solid substrate-bound ligand with a solution containing an antiligand under conditions and for a sufficient period of time to allow a ligand/antiligand complex to form. As stated above, if neither the ligand nor the antiligand is labeled, a labeled ligand can be also introduced under conditions and for a sufficient period of time to allow formation of a sandwiched complex (i.e., ligand/antiligand/labeled ligand complex). Since the ligand or antiligand is labeled, any complexes formed can be detected on the basis of the label in the complex.

The assays can be conducted in a variety of ways. One approach involves attaching the ligand of interest to the solid substrate surface and contacting the solid substrate-bound ligand with a solution containing antiligands. Antiligands that do not form complexes are washed away under conditions such that complexes that are formed remain immobilized to the solid substrate. The detection of complexes immobilized to the solid substrate can be accomplished in a number of ways. If the non-immobilized antiligand is labeled, the detection of label antiligand immobilized on the solid substrate indicates that a ligand/antiligand complex has been formed. If, however, the non-immobilized antiligand is not labeled, complexes can nonetheless be detected by indirect means. For instance, a labeled ligand that specifically binds to the antiligand can be utilized to detect complexes anchored to the solid substrate, e.g., ELISA, FLISA, etc.

Alternatively, ligands and antiligands can be contacted in solution. Complexes can then be separated from uncomplexed ligands and antiligands and complexes detected. One approach for conducting such an assay is to contact an antiligand of interest with a test solution potentially containing a ligand that binds to the antiligand. The resulting mixture can then be contacted with a solid substrate-bound antibody that specifically binds to the antiligand to immobilize any complexes that have been formed. Labeled antibodies specific for the antiligand can then be contacted with any immobilized complexes to detect the presence of such complexes.

The ligand (antiligand) attached to the flow channel can be attached directly to the solid substrate surface or via a linker. In general, the solid substrate surface and the ligand (antiligand) being attached to the surface need appropriate chemical functionality such that the functional groups borne by these two entities can react with one another and become attached. Often the attachment is achieved by formation of a covalent bond between the binding pair member and surface, although electrostatic, hydrogen bond interactions and hydrophobic interactions can also act to attach the binding pair member and surface.

A variety of linkers can be utilized to attach the ligand (antiligand) to the solid substrate surface. The linkers typically are polyfunctional, preferably bifunctional, with a functional group at one end able to react with a functional group on the solid substrate surface and a functional group on the other end able to react with a functional group borne by the ligand (antiligand) to be attached to the solid substrate surface. The functional groups at each end of such linkers can be the same or different. Examples of suitable linkers include straight or branched-chain carbon linkers, heterocyclic linkers and peptide linkers. Exemplary linkers that can be employed are available from Pierce Chemical Company in Rockford, Ill. and are described in EPA 188,256; U.S. Pat. Nos. 4,671,958; 4,659,839; 4,414,148; 4,669,784; 4,680, 338, 4,569, 789 and 4,589,071, Eggenweiler, H. M, Drug Discovery Today 1998, 3, 552, all of which are incorporated herein by reference in their entirety.

Other linkers include members of a binding pair. In this arrangement, one binding pair member is attached to the solid substrate surface. The other member of the binding pair is attached to the ligand (antiligand) one seeks to attach to the solid substrate surface. Exemplary binding pair members include biotin/avidin (or streptavidin) and antigen/antibody.

Depending upon the composition of the solid substrate, it sometimes is necessary to derivatize the solid substrate surface so that the binding pair member can be attached. As described supra, a variety of agents can be used to derivatize the solid substrate surface. Examples include, but are not limited to, silanizing reagents (e.g., 3-aminopropyltriethoxysilane, N-(2-aminoethyl)-3-aminopropyltrimethoxysilane, dimethylchlorosilane or hexamethyldisilazane).

3. Assays for Compounds that Inhibit Binding Interactions

The microfluidic devices can also be utilized in a competitive formats to identify agents that inhibit the interaction between known binding partners. Such methods generally involve preparing a reaction mixture containing the binding partners under conditions and for a time sufficient to allow the binding partners to interact and form a complex. In order to test a compound for inhibitory activity, the reaction mixture is prepared in the presence (test reaction mixture) and absence (control reaction mixture) of the test compound. Formation of complexes between binding partners is then detected, typically by detecting a label borne by one or both of the binding partners. The formation of more complexes in the control reaction then in the test reaction mixture at a level that constitutes a statistically significant difference indicates that the test compound interferes with the interaction between the binding partners.

The order of addition of reactants can be varied to obtain different binding information concerning the compounds being tested. For example, test compounds that interfere with the interaction between binding pair members can be identified by conducting the reaction in the presence of the test compound, i.e., by introducing the test compound into the reaction mixture prior to or simultaneously with the binding pair members. Alternatively, test compounds capable of disrupting preformed complexes can be identified by adding the test compound to the reaction mixture after the complexes have been formed. This latter type analysis enables one to identify compounds that have a higher binding constant then one of the members of the binding pair and thus is able to displace that binding pair member from the complex.

4. Immunological Assays

Immunological assays are one general category of assays that can be performed with the microfluidic devices provided herein. Certain assays are conducted to screen a population of antibodies for those that can specifically bind to a particular antigen of interest. In such assays, a test antibody or population of antibodies is contacted with the antigen which is attached to the solid substrate surface. Other assays are conducted to examine a sample to determine if an analyte of interest is present by detecting binding between an antibody that specifically recognizes the analyte and the analyte. In assays such as this, often it is the antibody that is attached to the solid substrate surface and a solution containing potential antigens contacted with the immobilized antibody. In both types of assays, however, either the antigen or antibody can be immobilized.

Sandwich Assay

Immunological assays can be conducted in a variety of different formats. For example, the assays can involve direct binding between antigen and antibody, the so-called sandwich assay, enzyme linked immunosorbent assays (ELISA), fluorescent linked immunosorbent assays (FLISA), and competitive assays. In an ELISA or FLISA assay, for example, a capture antibody that specifically binds to the analyte of interest is attached to the solid substrate surface. A solution potentially containing the analyte of interest is then introduced into the first or the second flow channels and contacted with the immobilized capture antibody to form a binary complex. A second antibody (a detection antibody) that recognizes another portion of the analyte than the capture antibody is then contacted with the binary complex through the other flow channels to form a ternary complex at the channel intersection areas. The detection antibody includes an assayable enzyme or a fluorescent label.

In ELISA, formation of the ternary complex can be detected by introducing the appropriate enzyme substrate into the flow channel and allowed to contact any ternary complex. Signal produced in association with the enzyme catalyzed formation of product is detected by the detector.

In FLISA, formation of the ternary complex can be detected by observing fluorescence at the channel intersecting areas. The fluorescent label can be covalently bonded to one of the ligands, thus forming a labeled ligand moiety, or a fluorescent tag can be added to the ternary complex to form a tagged complex. Fluorescence can be detected after removing the elastomeric layer from the solid substrate or with the elastomeric layer in tact.

As discussed supra, capture antibodies can be attached to the solid substrate surface via functional groups borne by the antibody (e g, amino, carboxyl, sulfhydryl, hydroxyl) and complementary groups on the solid substrate surface or introduced by derivatization.

B. Antimicrobial Assays

By contacting various microbial cells with different test compounds, one can also utilize the devices provided herein to conduct antimicrobial assays, thereby identifying potential antibacterial compounds. The term "microbe" as used herein refers to any microscopic and/or unicellular fungus, any bacteria or any protozoan. Some antimicrobial assays involve immobilizing a cell on the solid substrate surface and contacting it with at least one potential antimicrobial compound. The effect of the compound can be detected as any detectable change in the health and/or metabolism of the cell. Examples of such changes, include but are not limited to, alteration in growth, cell proliferation, cell differentiation, gene expression, cell division and the like.

The following examples are provided to further illustrate certain aspects of the invention, but are not to be construed so as to limit the scope of the invention.

EXAMPLES

Example 1

This example illustrates a method for producing a 4-layer microfluidic device having protein A (*Staphylococcus aureus* $F_c$ binding protein) on its surface. The 4-layer device enables an assay to be performed at a precise location on a given solid substrate.

A fluid flow channel mold was prepared by spinning Shipley 5740 at 3600 rpm for 30 sec, soft baking for 60 s at 105° C. (measured thickness=7.8 μm), and hardbaking at 140° C. for 150 sec. (final mold thickness=10 μm). A control channel mold was prepared by spinning shipley 5740 at 850 rpm for 30 sec, followed by 5 min rest period prior to soft baking for 180 sec at 105° C. (final mold thickness=20 μm). A via mold was prepared by spinning AZ PLP 100-XT at 1240 rpm for 30 sec. followed by soft baking for 8 min at 95° C. (final mold thickness=35 μm).

Figure 8B:
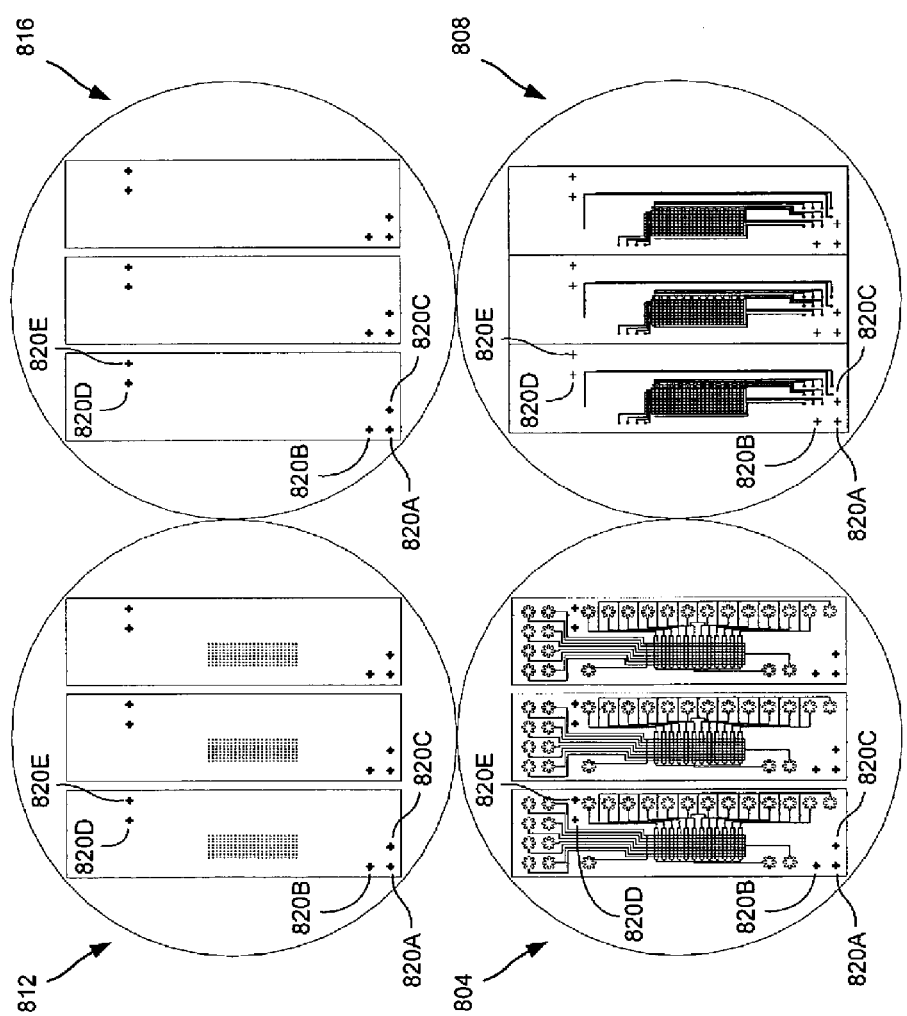
Figure 8C:
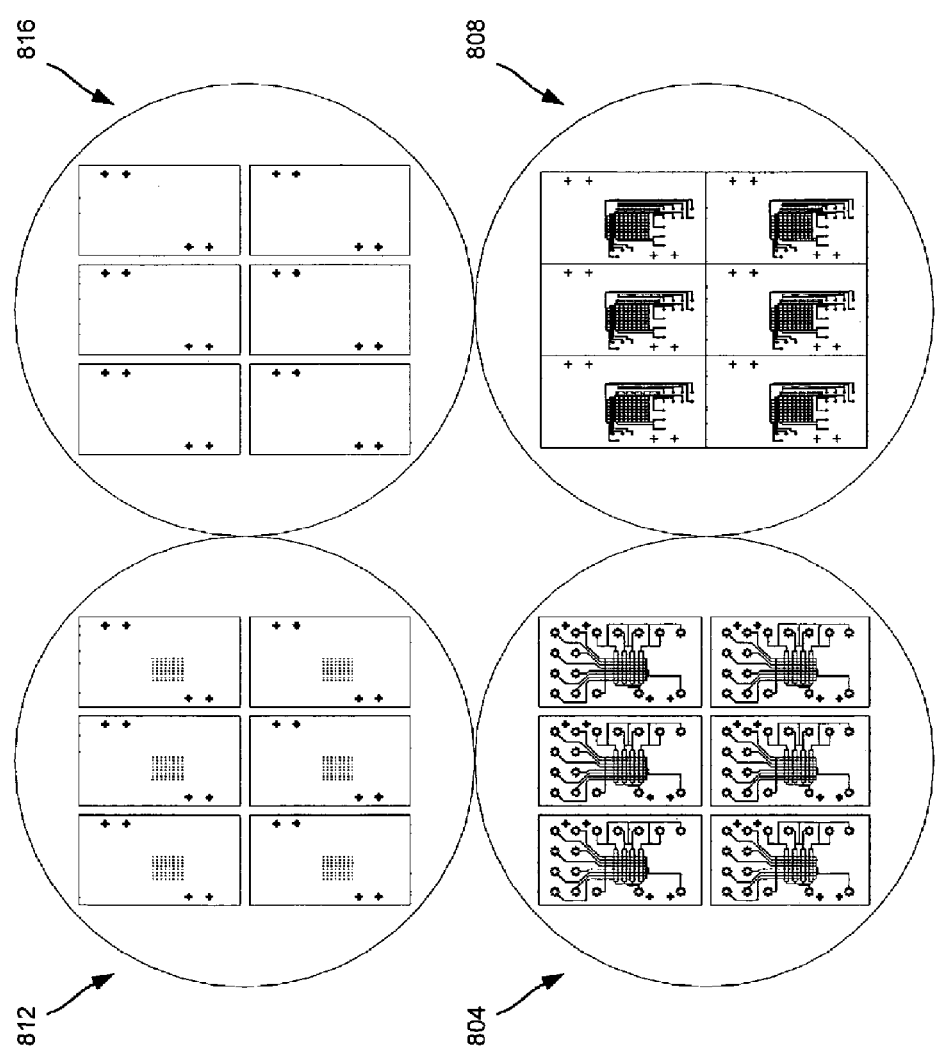
Figure 8D:
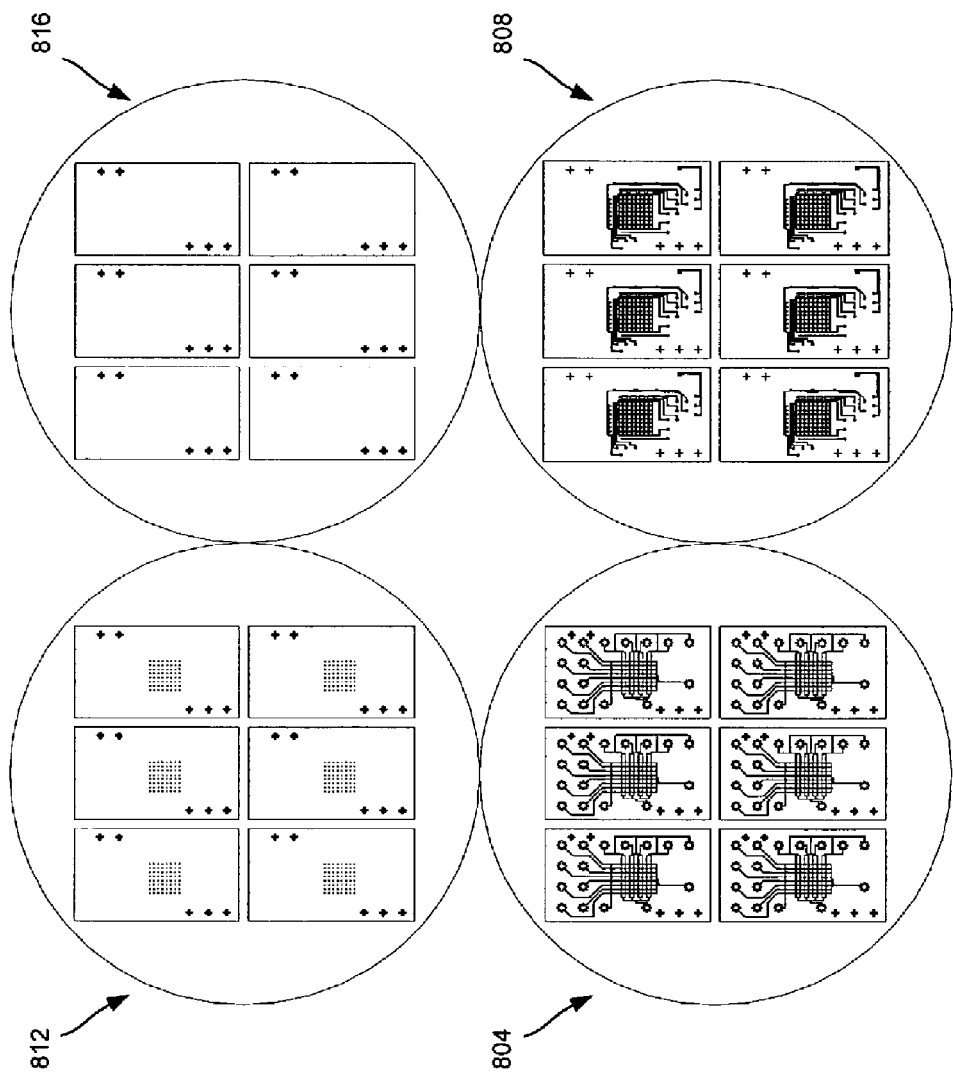
Figure 8E:
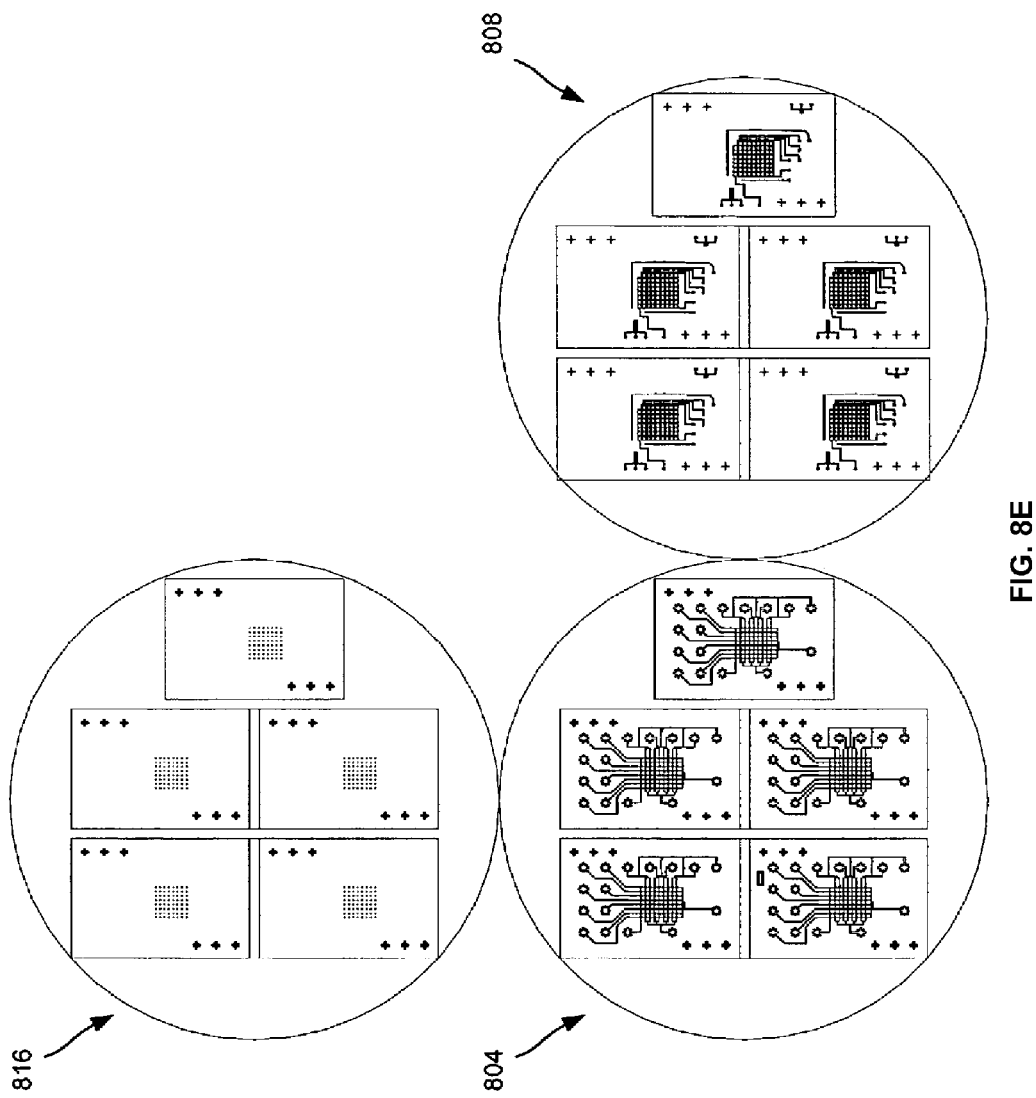

Exemplary mold designs for each of the corresponding control layer (808), the fluid (i.e., flow channel) layer (804), and the via layer (812) are shown in FIGS. 8A-E. In FIGS. 8B-D, an alignment mask 816 is also shown. Alignment mask 816 and each of the layers also includes alignment guides 820a-e, which aids in aligning each layers properly.

PDMS Process

Elastomeric layer was prepared as follows:
1) Mix 30:1 PDMS GE 615: 30 g part A, 1 g part B
   mix components at 1000 rpm under vacuum.
2) TMCS (trimethylchlorosilane) vapor treat all three molds for 3 min.
3) Spin mixed 30:1 PDMS on the fluid channel mold at 1090 rpm for 200 sec.
   PDMS thickness is 35 μm
   Oven bake wafer at 80° C. for 30 min
4) Mix 4:1 PDMS GE 615: 80 g part A, 20 g part B
   mix components at 1000 rpm under vacuum
5) Pour 4:1 PDMS on control channel mold
   Oven bake wafer at 80° C. for 30 min
6) Mix 30:1 PDMS GE 615: 30 g part A, 1 g part B
   mix components at 1000 rpm under vacuum.
7) Spin 30:1 PDMS on the via mold at 1260 rpm for 200 sec
   PDMS thickness is 30 μm (5 μm thinner than mold)
   Oven bake wafer at 80° C. for 1.5 hrs
8) Peel off PDMS from the control channel mold
   Dice PDMS slab along chip borders
   Punch PDMS chip at pneumatic fill marks on chip
9) Align diced PDMS chips on to the fluid control mold
   Oven bake at 80° C. for 1 hr.
10) Score PDMS along chip borders on the control channel mold
11) Peel 2 layer chips off of the control channel mold
12) Align 2 layer chips on the via mold
    Oven bake at 80° C. for 3 hrs.
13) Score PDMS along chip borders on the via mold
14) Peel 3 layer chips off of the via mold Substrate Bonding A solid substrate was prepared as follows:
1) prepare protein A slide
   nitrogen dry protein A slides after removal from 4° C. refrigerator.
2) Place PDMS in a central position on the protein A slide.
3) Oven bake at 80° C. for 30-45 min
4) Allow chip to cool to room temp. before adding PBST.
5) Pipette in any well 0.5% PBST solution.

This device shields the samples and reagents from the substrate except where the chemistry is to be performed on the substrate. This shielding helps preserve the sample/reagent concentration by preventing immobilization upstream of the intended assay site. In addition, this device facilitates the loading of the device and increases the bonding area between the device and the substrate. This $3^{rd}$ (i.e., via) layer effectively seals the chip and renders the substrate bonding independent of the fluidic network feature density. Molds are fabricated for each of the three layers of the device. The first two molds are that of the control and fluid layer and comprise the standard 2-layer fluidic device. The additional $3^{rd}$ mold is that of the via layer where posts of various shapes are patterned. The height of this mold is about 5 μm higher than the PDMS spun on the mold. The 2 layer chip is assembled and is aligned to the $3^{rd}$ layer. Once the 3-layer chips is cured, the chip is dry etched from the via layer side to open the vias as residual PDMS may exist on the mold during the spinning step. See FIG. 9. Etching of the PDMS is done with a 2:1 mixture of $C_2F_6$ and $O_2$ at 400 watts for 10-20 min.

Figure 10A:
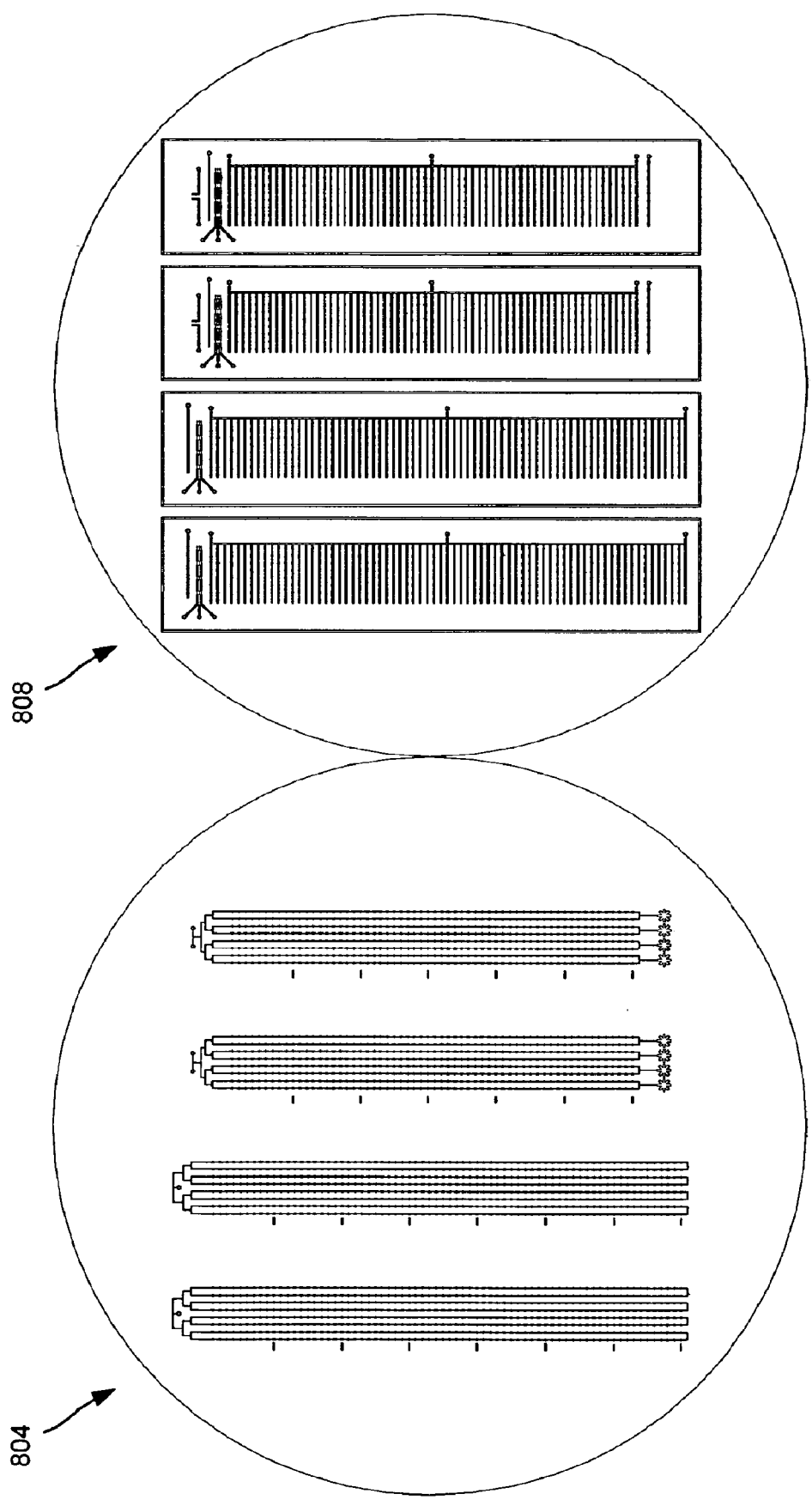
FIGS. 10A and 10B also shows exemplary designs for fluid layer (804) and the control layer (808).
Figure 10B:
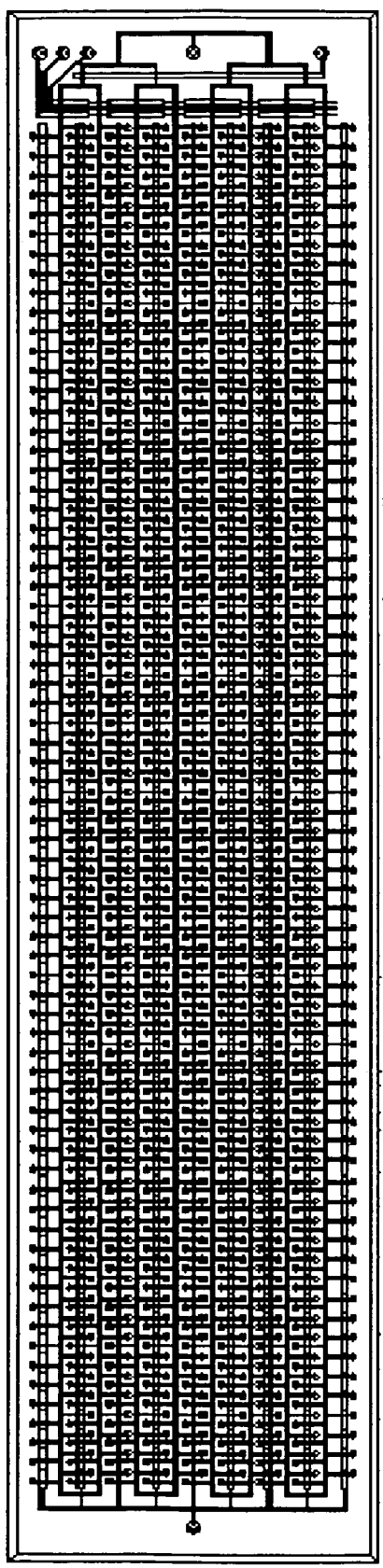

While the above example is illustrated for producing a three-layer elastomeric material comprising a via layer, by eliminating the via layer a two-layer elastomeric material can also be produced using the process described above. Thus, by using only the fluid layer mold 804 and the control layer mold 808, microfluidic devices having two-layer elastomeric material (which forms a monolithic structure when cured) can be prepared. This monolithic elastomeric layer is then attached directly to the solid substrate surface for assaying. Another two-layer monolithic elastomeric layer design and the corresponding micrfluidic device that is fabricated is shown in FIGS. 10A and 10B.

It should be noted that while the via layer is not required, it provides a distinct areas on the solid substrate surface that are exposed to the assaying conditions. This is particularly useful when the amount of sample available is extremely minute.

Example 2

This example illustrates a method for using a microfluidic device of the present invention for conducting a FLISA assay.

Figure 11:
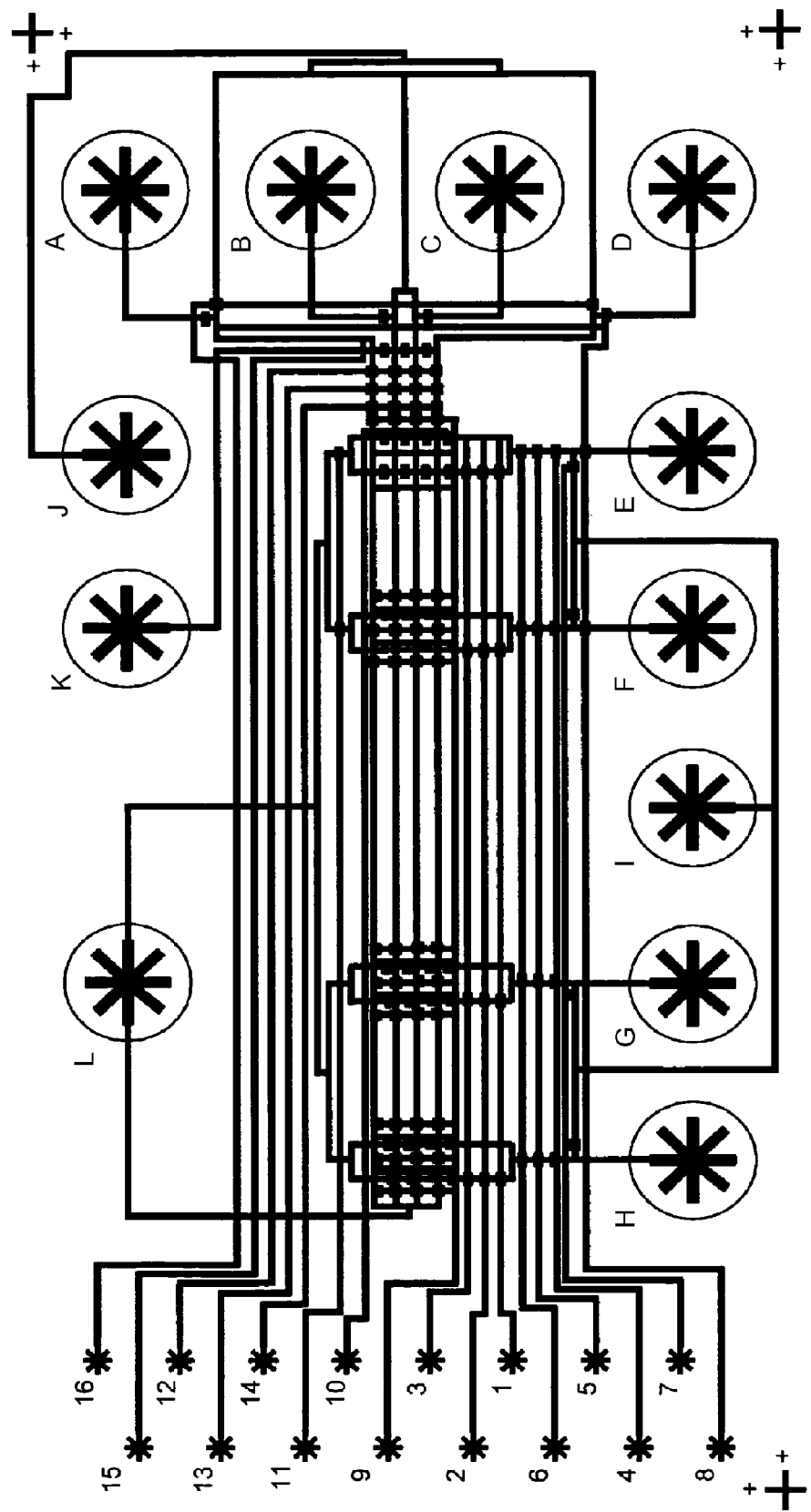
FIG. 11 shows a microfluidic device configuration used in Example 2.

Using a microfluidic device of configuration shown in FIG. 11, various assays were conducted as follows:

Fluid Inputs

Fluid inputs A, B, C, and D are the reagent inlets. Through these inlets solutions of reagents, such as an antibody, can be added. When the proper valves are actuated, fluid flow from these inputs are directed into discrete areas of the chip. Fluid inputs E, F, G, and H are the sample inlets. Through these inlets solutions of reagents, such as analytes or antigens, can be added. When the proper valves are actuated, fluid flow from these inputs are directed into discrete areas of the chip. Fluid input I is a common wash inlet. This input connects to fluid lines adjacent to fluid inputs E-H. It may contain buffers or solutions common to all samples. It can also contain a buffers or solution to block the channel walls or block the substrate surface. Fluid input J is a common wash inlet. This input connects to fluid lines adjacent to fluid inputs A-D. It may contain buffers or solutions common to all samples. It can also contain a buffers or solution to block the channel walls or block the substrate surface. Fluid input K is a common wash inlet. This input connects to fluid lines adjacent to fluid inputs A-D. It may contain buffers or solutions common to all samples. It can also contain a buffers or solution to block the channel walls or block the substrate surface. Fluid input L is a common waste inlet. This connects to common lines through which fluid flow is directed.

Any and all of the inlets can be used to prime the chip, by wetting the channel and the substrate.

Control Valves

Control valves are actuated at 12-16 psi. Positive displacement fluidic pumps are activated at 60 Hz (10 Hz per step of the cycle). Valves 1, 2, and 3 control a recirculating pump. When activated, the valves pump fluid clockwise around the reaction area. Valves 4, 5, and 6 control a sample through pump. When activated, the valves pump fluid from fluid inputs E, F, G, and H, or from fluid input I, into the reaction area. Valve 7 controls the isolation of solutions in fluid input I. Actuating the valve prevents a solution in fluid input I from entering the reaction area. Opening the valve allows a solution from fluid input I into the reaction area. Valve 8 controls the isolation of solutions in fluid inputs A, B, C, D, E, F, G, and H. Actuating the valve prevents samples and reagents from entering the reaction area from fluid inputs A, B, C, D, E, F, G, and H. Opening the valve allows samples and reagents into the reaction area from fluid inputs A, B, C, D, E, F, G, and H. Valve 9 controls the isolation of sample in the reaction area. Actuating the valve prevents fluid flow in the reaction area in a vertical direction. When used in conjunction with the recirculating pump (valves 1, 2, and 3) or the sample through pump (valves 4, 5, and 6), flow through the reaction area occurs only horizontally. Valve 10 controls the isolation of reagents in the sample area. Actuating the valve prevents fluid flow in the reaction area in a horizontal direction. When used in conjunction with the reagent through pump (valves 12, 13, and 14), flow through the reaction area occurs only vertically. Valve 11 controls the isolation of the entire reaction area. Actuating the valve prevents flow out of the reaction area. Actuating the valve also prevents flow into the reaction area from fluid input L. Valves 12, 13, and 14 control a reagent through pump. When activated, the valves pump fluid from fluid inputs A, B, C, and D, or fluid input J, or fluid input K, into the reaction area. Valve 15 controls the isolation of fluid input J. Actuating the valve prevents a solution from fluid input J from entering the reaction area. Valve 16 controls the isolation of fluid input K. Actuating the valve prevents a solution from fluid input K from entering the reaction area.

Protocol for the Protein Microprocessor Chip

Figure 12:
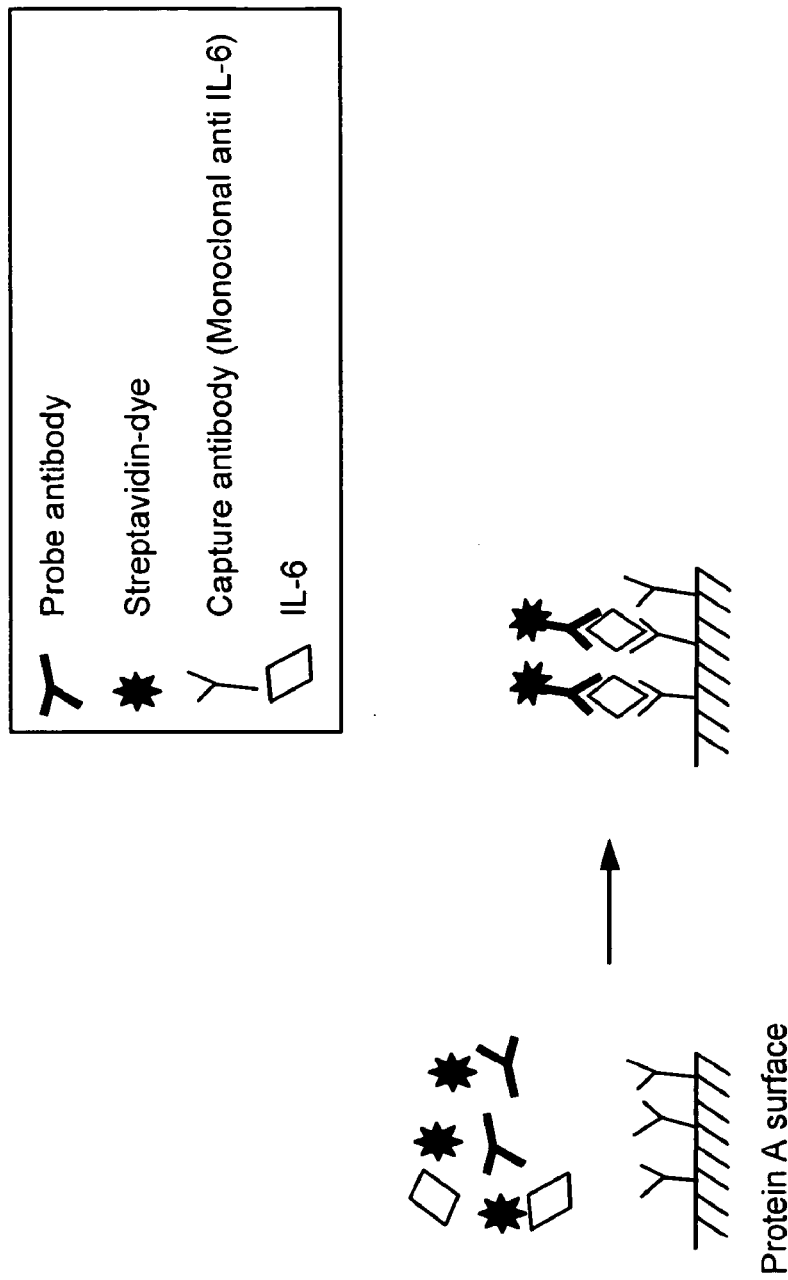
FIG. 12 is a schematic illustration of a binding assay described in Example 2.

The assay can detect antigens, such as the detection of human interleukin-6 (IL-6). As schematically illustrated in FIG. 12, the assay is a sandwich assay, which uses an immobilized mouse anti-human IL-6 monoclonal capture antibody (mAb) and a biotinylated polyclonal probe antibody Immobilization of the probe antibody is dependent upon binding of IL-6 in the sample to the capture antibody. Dye-conjugated streptavidin is bound to the biotinylated antibody and bound fluorescence quantified.

FLISA Scheme

In order to promote binding of the monoclonal antibody to the glass surface in an appropriate orientation to permit presentation of the antigen binding site to the solvent, *Staphylococcus aureus* Protein A derivatized slides are used. Protein A is a 42KD antibody-binding protein that binds the Fc (constant region) portion of the molecule. One protein A molecule can bind up to 4 molecules of capture antibody. The chemistry of Protein A binding to antibody is well known to one skilled in the art.

Using the Chip

1) The chip is baked onto a Protein A glass substrate for 30-45 minutes at 80° C. The chip on the glass substrate is cooled to room temperature. It is then primed by the addition of an appropriate aqueous solution. The fluidic (i.e., flow) layer is filled with phosphate buffered saline (PBS) containing 0.5% (v/v) Tween-20. In a typical use, the following solutions are prepared:

| Reagent (producing organism) | Stock Concentration | Stoichiometry | S1: 5 ng/mL IL6 | S2: 2.5 ng/mL IL6 | S3: 1 ng/mL IL6 | S4: blank (0 ng/mL) |
|---|---|---|---|---|---|---|
| biotinylated polyclonal anti-IL6 (goat) | 50 µg/mL | at least 3 eq | 2.2 µL | 2.2 µL | 2.2 µL | 0 µL |
| recombinant IL6 | 10 µg/mL | | 0.5 µL | 0.25 µL | 0.1 µL | 0 µL |
| Cy5 labeled streptavidin | 1 mg/mL | at least 45 eq | 1 µL | 1 µL | 1 µL | 0 µL |
| dinitrophenyl-Keyhole Limpet hemocyanin | 10 µg/mL | 5 ng/mL | 0.5 µL | 0.5 µL | 0.5 µL | 0.5 µL |
| Alexa-Fluor 488 anti-dinitrophenyl Keyhole Limpet Hemocyanin (rabbit) | 2 mg/mL | 2 µg/mL | 1 µL | 1 µL | 1 µL | 1 µL |
| Rabbit whole serum | 60 mg/mL | 1 mg/mL | 16.67 µL | 16.67 µL | 16.67 µL | 16.67 µL |
| PBS w/0.1% Tween-20 (PBST) | | to 1 mL | 978 µL | 978 µL | 979 µL | 982 µL |

In addition: the following reagents are prepared.

R1. 1 mg/mL Rabbit serum in PBST

R2. 250 µg/mL monoclonal anti-IL6 (mouse), 2.5 µg/mL anti-dinitrophenyl keyhole limpet hemocyanin (rabbit) in PBST R3. 250 µg/mL monoclonal anti-IL6 (mouse), 2.5 µg/mL anti-dinitrophenyl keyhole limpet hemocyanin (rabbit) in PBST R4. 250 µg/mL monoclonal anti-IL6 (mouse), 2.5 µg/mL anti-dinitrophenyl keyhole limpet hemocyanin (rabbit) in PBST Wash Solutions:

W1. 1 mg/mL rabbit serum in PBST

W2. 1 mg/mL rabbit serum in PBST

W3. 10 µg/mL Cy3 conjugated anti-mouse IgG (goat) in PBST.

2) Excess buffer is pipetted out of fluid inlets A, B, C, D, E, F, G, H, I, and J. Valves 7, 8, 15, and 16 are actuated to close off fluid inlets A, B, C, D, E, F, G, H, I, J, and K. Reagent solutions R1, R2, R3, and R4 are added to fluid inlets A, B, C, and D, respectively. Sample solutions S1, S2, S3, and S4 are added to fluid inlets E, F, G, and H, respectively. Wash solution W1 is added to fluid inlet I. Wash solution W2 is added to fluid inlet J. Wash solution W3 is added to fluid inlet K.

3) Reagents are then pumped into the chip. Valves 10 and 11 are actuated to allow for only vertical flow through the reaction area. Valve 8 is opened to allow for solutions in fluid inlets A, B, C, and D to flow into the reaction area. The reagent through pump (valves 12, 13, and 14) is activated to direct flow to the reaction area in a vertical direction. The pump is run for 10-20 minutes.

4) The reaction area is washed with vertical flow. Valve 8 is actuated to prevent further flow of solutions from fluid inlets A, B, C, and D into the reaction area. Valve 16 is opened to allow the solution in fluid inlet J to flow through the reaction area in a vertical direction. The reagent through pump (valves 12, 13, and 14) is activated to direct flow to the reaction area in a vertical direction. The pump is run for 5-10 minutes (generally one half the time of step 3).

5) The reagent through pump (valves 12, 13, and 14) is stopped and valves 12, 13, and 14 are opened. Valve 16 is actuated to prevent the solution in fluid inlet J from flowing into the reaction area. Valve 8 remains actuated to prevent flow of solutions from fluid inlets E, F, G, and H into the reaction area. Valve 9 is actuated to cause flow to occur through the reaction area in a horizontal direction. Valve 10 is opened to allow flow to occur in a horizontal direction. Valve 11 is opened to allow horizontal flow to occur through the reaction area to the fluid inlet L. Valve 7 is opened to allow the solution in fluid inlet I to flow through the reaction area in a horizontal direction. The sample through pump (valves 4, 5, and 6) is activated to direct flow to the reaction area in a horizontal direction. The pump is run for 5-10 minutes.

6) Valve 7 is actuated to prevent the solution in fluid inlet I from flowing into the reaction area. Valve 8 is opened to allow the solutions in fluid inlets E, F, G, and H to flow into the reaction area in a horizontal direction. Valve 11 is opened to allow flow to occur through the reaction area to the fluid inlet L. The sample through pump (valves 4, 5, and 6) is activated to direct flow to the reaction area in a horizontal direction. The pump is run for 5 minutes.

7) The sample through pump (valves 4, 5, and 6) is stopped and valves 4, 5, and 6 are opened. Valve 11 is actuated to prevent flow through the reaction area to the fluid inlet L. The recirculating pump (valves 1, 2, and 3) is activated to direct flow around the reaction area in a clockwise direction. The pump is run for 30 minutes.

8) Steps 6) and 7) can be repeated to allow for repeated samplings of solutions from fluid inlets E, F, G, and H into the reaction area.

9) The recirculating pump (valves 1, 2, and 3) is stopped and valves 1, 2, and 3 are opened. Valve 8 is actuated to prevent the solutions in fluid inlets E, F, G, and H from flowing into the reaction area in a horizontal direction. Valve 11 is opened to allow flow through the reaction area to the fluid inlet L. The sample through pump (valves 4, 5, and 6) is activated to direct flow to the reaction area in a horizontal direction. The pump is run for 5-10 minutes.

10) The sample through pump (valves 4, 5, and 6) is stopped and valves 4, 5, and 6 are opened. Valves 10 and 11 are actuated to allow for only vertical flow through the reaction area. Valve 9 is opened to allow for flow into the reaction area in a vertical direction. Valve 15 is opened to allow the solution in fluid inlet K to flow into the reaction area. The reagent through pump (valves 12, 13, and 14) is activated to direct flow to the reaction area in a vertical direction. The pump is run for 5-10 minutes.

11) At the end of the procedure, valves 10, 11, 12, 13, and 14 are opened. The chip can be removed from the substrate at this point.

The pneumatic connections to the control layer of the chip are removed. The chip and substrate are submerged in a solution of PBS. The chip is removed and the substrate is washed with three five-minute washes with fresh PBS. The slide is dried and imaged in a fluorescence microarray scanner with at least three filter sets to determine the signal from AlexaFluor 488, Cy3, and Cy5.

Incorporated herein by reference in its entirety is attached Appendix A comprising 15 pages of brief summary of some of the aspects of the present invention.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes to the same extent as if each individual publication, patent or patent application were specifically and individually indicated to be so incorporated by reference.

What is claimed is:

1. A microfluidic device comprising:
a solid substrate surface;
a plurality of first flow channels;
a plurality of second flow channels,
wherein the plurality of first flow channels and the plurality of second flow channels are adapted to allow the flow of a solution therethrough,
wherein each of the plurality of second flow channels intersect each of the first flow channels to define a plurality of intersecting areas formed at intersections between each of the plurality of first flow channels and each of the plurality of second flow channels, and
wherein at least some of the plurality of intersecting areas are in fluid communication with the solid substrate surface;
a plurality of loop forming control valves, each of the plurality of loop forming control valves configured to close a section of the plurality of second flow channels to thereby form a plurality of closed loop flow channels; and
a recirculating pump operatively disposed with respect to one of the plurality of closed loop flow channels and configured to recirculate the solution through the one of the plurality of closed loop flow channels.

2. The microfluidic device of claim 1 further comprising a peristaltic pump having a plurality of pump valves and operative to pump the solution through the one of the plurality of second flow channels, wherein at least one of the plurality of pump valves comprises a control valve of the plurality of loop forming control valves.

3. The microfluidic device of claim 2 wherein the recirculating pump and the peristaltic pump are both configured to pump the solution through one of the plurality of second flow channels.

4. The microfluidic device of claim 1 wherein each of the plurality of loop forming control valves comprises a loop forming control channel and an elastomeric segment that is deflectable into or retractable from a second flow channel of the plurality of second flow channels upon which the loop forming control valve operates in response to an actuation force applied to the loop forming control channel, the elastomeric segment when positioned in the second flow channel restricting solution flow therethrough thereby forming the closed loop flow channel.

5. The microfluidic device of claim 1 further comprising:
a plurality of first control valves each operatively disposed with respect to each of the plurality of first flow channels to regulate flow of the solution through each of the plurality of first flow channels, wherein each of plurality of the first control valves comprises a first control channel and an elastomeric segment that is deflectable into or retractable from a first flow channel of the plurality of first flow channels upon which the first control valve operates in response to an actuation force applied to the first control channel, the elastomeric segment when positioned in the first flow channel restricting solution flow therethrough; and
a plurality of second control valves each operatively disposed with respect to each of the plurality of second flow channel to regulate flow of the solution through the second flow channels, wherein each of the plurality of second control valves comprises a second control channel and an elastomeric segment that is deflectable into or retractable from the second flow channel of the plurality of second flow channels upon which the second control valve operates in response to an actuation force applied to the second control channel, the elastomeric segment when positioned in the second flow channel restricting solution flow therethrough.

6. The microfluidic device of claim 5 wherein actuation of both of the plurality of first control valves and the plurality of second control valves forms a plurality of holding valves, each of which is operatively disposed with respect to each of the plurality of first flow channels and each of the plurality of second flow channels such that a holding space encapsulating each of the plurality of intersecting areas is formed.

7. The microfluidic device of claim 1 wherein the recirculating pump comprises more than one control channel separated from the plurality of closed loop flow channels by an elastomeric segment that is deflectable into the one of the plurality of closed loop flow channels in response to an actuation force.

8. The microfluidic device of claim 1 further comprising a solution inlet for each of the first flow channels in fluid communication therewith for introduction of a first solution.

9. The microfluidic device of claim 8 further comprising a first solution outlet for each of the first flow channels in fluid communication therewith for output of at least the first solution.

10. The microfluidic device of claim 8 further comprising a second solution inlet for each of the second flow channels in fluid communication therewith for introduction of a second solution.

11. The microfluidic device of claim 10 further comprising a second solution outlet channel for each of the second flow channels in fluid communication therewith for output of at least the second solution.

12. The microfluidic device of claim 1 further comprising an elastomeric layer, wherein the plurality of first flow channels and the plurality of second flow channels are at least partially defined by an interface between the solid substrate surface and the elastomeric layer.

13. The microfluidic device of claim 1 further comprising an elastomeric layer, wherein the plurality of first flow channels and the plurality of second flow channels are located within the elastomeric layer, and wherein each of the plurality of intersecting areas define an opening in the elastomeric layer that is in fluid communication with the solid substrate surface thereby forming a well that is adapted to collect a fluid therein.

14. The microfluidic device of claim 1 further comprising a plurality of first flow channel pumps, wherein each of the plurality of first flow channel pumps is operatively disposed with respect to one of the first flow channels to regulate the flow of solution through each of the first flow channels.

15. The microfluidic device of claim 14 further comprising a plurality of second flow channel pumps, wherein each of the second flow channel pumps is operatively disposed with respect to one of the second flow channels such that solution flow through each of the second flow channels can be regulated by one of the pumps.

16. The microfluidic device of claim 15 wherein each of the plurality of second flow channel pumps comprises more than one control channel each separated from the flow channel by an elastomeric segment which is deflectable into the flow channel in response to an actuation force.

17. The microfluidic device of claim 1 further comprising a solid support surface having a ligand that is capable of specifically binding to an anti-ligand at each of the intersecting areas.

18. The microfluidic device of claim 17 further comprising a plurality of fluid pumps, wherein each second flow channel of the plurality of second flow channels is in fluid communication with a fluid pump of the plurality of fluid pumps, to transport solution through the second flow channel under the action of the fluid pump.

19. The microfluidic device of claim 18 wherein the fluid pump comprises a plurality of control channels, wherein each control channel of the plurality of control channels is separated from the second flow channel by an elastomeric segment that is deflectable into the second flow channel in response to an actuation force.

20. The microfluidic device of claim 1 further comprising an elastomeric layer, wherein the solid substrate surface is capable of attaching a ligand and/or anti-ligand, and wherein the plurality of first flow channels, the plurality of second flow channels, the plurality of loop forming control valves, and the recirculating pump are at least partially disposed within the elastomeric layer.

21. The microfluidic device of claim 1, wherein the solid substrate surface is a layer.

22. The microfluidic device of claim 1, wherein the solid substrate surface is derivatized to provide carboxyl sites.

23. The microfluidic device of claim 1, wherein the solid substrate surface comprises a solid-substrate bound ligand.

24. The microfluidic device of claim 23, wherein the solid-substrate bound ligand binds an anti-ligand, and wherein the anti-ligand is an oligonucleotide.

25. A microfluidic device comprising:
a solid substrate surface;
a plurality of first flow channels;
a plurality of second flow channels;
  wherein the plurality of first flow channels and the plurality of second flow channels are adapted to allow the flow of a solution therethrough; and
  wherein each of the plurality of second flow channels intersect each of the first flow channels to define a plurality of intersecting areas formed at intersections between each of the plurality of first flow channels and each of the plurality of second flow channels;
a plurality of directing control valves operatively disposed with respect to the plurality of first flow channels and the plurality of second flow channels, each of the plurality of directing control valves configured to direct fluid flowing through the plurality of first flow channels or fluid flowing through the plurality of second flow channels to the plurality of intersecting areas;
a plurality of loop forming control valves, each of the plurality of loop forming control valves configured to close a section of the plurality of second flow channels to thereby form a plurality of closed loop flow channels; and
a recirculating pump separate and distinct from the plurality of directing control valves and operatively disposed with respect to one of the plurality of closed loop flow channels and configured to recirculate the solution through the one of the plurality of closed loop flow channels.

26. The microfluidic device of claim 25, wherein the recirculating pump is separate and distinct from the plurality of loop forming control valves.

27. The microfluidic device of claim 25, wherein the plurality of loop forming control valves are separate and distinct from the plurality of directing control valves.

28. The microfluidic device of claim 25, wherein the recirculating pump is configured to recirculate the solution through the one of the plurality of closed loop flow channels when the plurality of directing control valves are configured to inhibit flow of the solution through the plurality of first flow channels and allow flow of the solution through the plurality of second flow channels in fluid communication with the one of the plurality of closed loop flow channels.

* * * * *